(12) United States Patent
Gregorich et al.

(10) Patent No.: US 7,404,823 B2
(45) Date of Patent: Jul. 29, 2008

(54) STENT CONFIGURATIONS

(75) Inventors: Daniel Gregorich, St. Louis Park, MN (US); Soo-Young Yoon, Maple Grove, MN (US); Michael P. Meyer, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 345 days.

(21) Appl. No.: 11/262,692

(22) Filed: Oct. 31, 2005

(65) Prior Publication Data

US 2007/0100434 A1    May 3, 2007

(51) Int. Cl.
    *A61F 2/06* (2006.01)
(52) U.S. Cl. ...................................... 623/1.15
(58) Field of Classification Search ....... 623/1.11–1.18; 606/194–196
    See application file for complete search history.

(56) References Cited

U.S. PATENT DOCUMENTS

| 5,776,161 | A | 7/1998 | Globerman | 606/194 |
|---|---|---|---|---|
| 5,876,449 | A | 3/1999 | Starck et al. | 623/23.7 |
| 5,911,754 | A | 6/1999 | Kanesaka et al. | 623/1.15 |
| 5,922,021 | A | 7/1999 | Jang | 623/1.15 |
| 6,113,627 | A | 9/2000 | Jang | 623/1.15 |
| 6,123,721 | A | 9/2000 | Jang | 623/1.15 |
| 6,193,747 | B1 | 2/2001 | Von Oepen | 623/1.15 |
| 6,200,334 | B1 | 3/2001 | Jang | 623/1.15 |
| 6,331,189 | B1 | 12/2001 | Wolinsky et al. | 623/1.15 |
| 6,348,065 | B1 | 2/2002 | Brown et al. | 623/1.16 |
| 6,409,761 | B1 | 6/2002 | Jang | 623/6.12 |
| 6,464,722 | B2 | 10/2002 | Israel et al. | 623/1.17 |
| 6,468,302 | B2 | 10/2002 | Cox et al. | 623/1.15 |
| 6,602,285 | B1 | 8/2003 | Von Oepen et al. | 623/1.17 |
| 6,730,116 | B1 | 5/2004 | Wolinsky et al. | 623/1.16 |
| 6,770,088 | B1 | 8/2004 | Jang | 623/1.16 |
| 6,776,794 | B1 * | 8/2004 | Hong et al. | 623/1.15 |
| 6,805,707 | B1 * | 10/2004 | Hong et al. | 623/1.16 |
| 2001/0056298 | A1 | 12/2001 | Brown et al. | 623/1.16 |
| 2002/0007212 | A1 | 1/2002 | Brown et al. | 623/1.16 |
| 2002/0095208 | A1 | 7/2002 | Gregorich et al. | 623/1.15 |
| 2002/0111669 | A1 | 8/2002 | Pazienza et al. | 623/1.15 |
| 2004/0267353 | A1 | 12/2004 | Gregorich | 623/1.16 |
| 2005/0015136 | A1 | 1/2005 | Ikeuchi et al. | 623/1.15 |

FOREIGN PATENT DOCUMENTS

| DE | 19840645 | 3/2000 |
|---|---|---|
| EP | 0 884 029 A1 | 12/1998 |
| EP | 0884029 A1 | 12/1998 |
| EP | 1378212 | 1/2004 |
| EP | 1437157 | 7/2004 |
| WO | WO 99/38457 | 8/1999 |
| WO | 00/42946 | 7/2000 |
| WO | WO 01/01885 | 1/2001 |
| WO | WO 01/01885 A1 | 1/2001 |
| WO | WO 01/41675 | 6/2001 |
| WO | 03/059207 | 7/2003 |
| WO | 2004/087015 | 10/2004 |

* cited by examiner

*Primary Examiner*—Suzette J Gherbi
(74) *Attorney, Agent, or Firm*—Vidas, Arrett & Steinkraus, P.A.

(57) ABSTRACT

A stent may comprise a plurality of serpentine bands, wherein adjacent serpentine bands are connected by at least one connector strut. A serpentine band may comprise alternating straight struts and s-shaped struts. Connector struts may comprise first connector struts and second connector struts, wherein the first connector struts are nonparallel to the second connector struts.

19 Claims, 31 Drawing Sheets

STENT CONFIGURATIONS

CROSS-REFERENCE TO RELATED APPLICATIONS

Not Applicable

STATEMENT REGARDING FEDERALLY SPONSORED RESEARCH

Not Applicable

FIELD OF THE INVENTION

Figure 1:
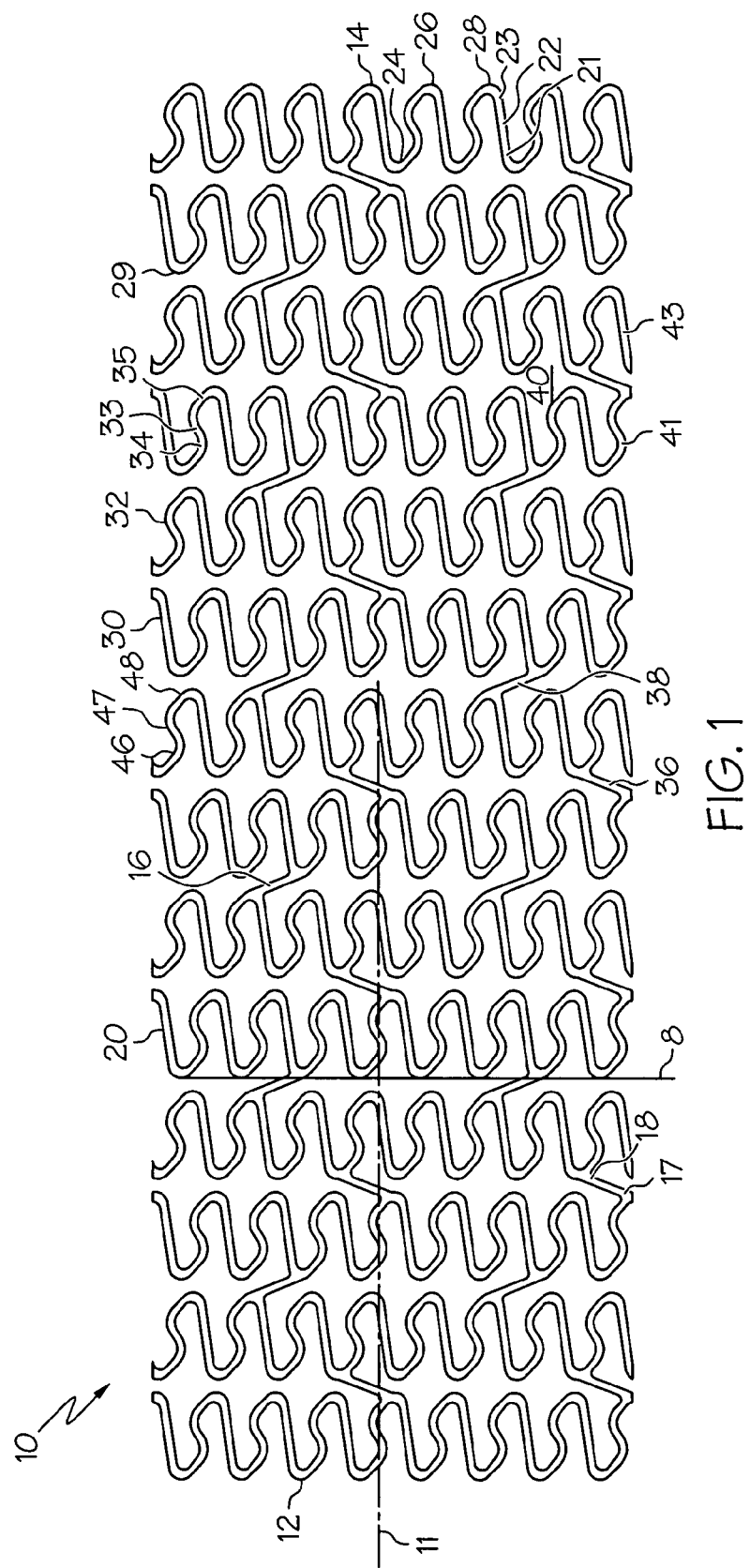

In some embodiments this invention relates to implantable medical devices, their manufacture, and methods of use. Some embodiments are directed to delivery systems, such as catheter systems of all types, which are utilized in the delivery of such devices.

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety. US 2004/0267353 and US 2002/0095208 are hereby incorporated herein by reference in their entireties.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a stent comprising a plurality of interconnected serpentine bands, each serpentine band having alternating straight struts and s-shaped struts forming peaks and valleys. Each straight strut is connected at one end to one s-shaped strut and at a second end to a second s-shaped strut. Each s-shaped strut is connected at one end to one straight strut and at a second end to a second straight strut. One end of the s-shaped struts is connected to one end of the straight struts at a peak, and another end of the s-shaped struts is connected to one end of the straight strut at a valley. Adjacent serpentine bands are connected by a plurality of linear connectors, the linear connectors extending from peaks of one band to valleys of band adjacent thereto.

In at least one other embodiment, a stent comprises a plurality of interconnected serpentine bands, each serpentine band having alternating straight struts and s-shaped struts forming peaks and valleys. Each straight strut is connected at one end to one s-shaped strut and at a second end to a second s-shaped strut. Each s-shaped strut is connected at one end to one straight strut and at a second end to a second straight strut. One end of the s-shaped struts is connected to one end of the straight struts at a peak and another end of the s-shaped struts connected to one end of the straight strut at a valley. Adjacent serpentine bands are connected by a plurality of linear connectors, the connectors extending from peaks of one band to valleys of a band adjacent thereto. The serpentine bands and connectors define a plurality of cells, each cell including a plurality of unconnected peaks and valleys. The unconnected peaks are disposed on one serpentine band, the unconnected valleys disposed on the adjacent serpentine band.

In at least one other embodiment, a stent comprises a plurality of interconnected serpentine bands, each serpentine band having alternating straight struts and s-shaped struts forming peaks and valleys. Each straight strut is connected at one end to one s-shaped strut and at a second end to a second s-shaped strut. Each s-shaped strut is connected at one end to one straight strut and at a second end to a second straight strut. One end of the s-shaped struts is connected to one end of the straight struts at a peak, and another end of the s-shaped struts is connected to one end of the straight strut at a valley. Adjacent serpentine bands are connected by a plurality of connectors, the connectors extending from peaks of one band to valleys of band a adjacent thereto. The connectors include a first connector extending in a first direction and a second connector extending in a second direction which is non-parallel to the first direction.

In at least one other embodiment, a stent comprises a plurality of interconnected serpentine bands, each serpentine band having alternating straight struts and s-shaped struts forming peaks and valleys. Each straight strut is connected at one end to one s-shaped strut and at a second end to a second s-shaped strut. Each s-shaped strut is connected at one end to one straight strut and at a second end to a second straight strut. One end of the s-shaped struts is connected to one end of the straight struts at a peak, and another end of the s-shaped struts is connected to one end of the straight strut at a valley. Adjacent serpentine bands are connected by a plurality of connectors, to form cells, cells which are circumferentially adjacent to one another being of different sizes.

In at least one other embodiment, a stent comprises a serpentine band, the serpentine band comprising a plurality of struts connected by alternating peaks and valleys. The struts include a plurality of lobed struts which have an outer surface, an inner surface and two sidewalls. One of the side walls is s-shaped, and the other sidewall has a different shape.

In at least one other embodiment, a stent comprises a plurality of serpentine bands, each serpentine band comprising a plurality of struts connected by turns. The turns comprise alternating peaks and valleys. The stent further comprises a plurality of connector struts. Adjacent serpentine bands are connected by at least one connector strut, each connector strut extending from a valley of one serpentine band to a peak of another serpentine band. A first serpentine band includes a plurality of first valleys and a second valley, wherein the first valleys are aligned about a circumference of the stent and the second valley is longitudinally offset from the first valleys. A second serpentine band includes a plurality of first peaks and a second peak, wherein the first peaks are aligned about a circumference of the stent and the second peak is longitudinally offset from the first peaks. A first connector strut is oriented at an angle to a stent lengthwise axis and connects between a first valley and a first peak. The second valley is longitudinally aligned with the first peak that is connected to the first connector strut and the second peak is longitudinally aligned with the first valley that is connected to the first connector strut.

In at least one other embodiment, a stent comprises a plurality of first serpentine bands and a plurality of second serpentine bands. Each first serpentine band includes a plurality of straight struts connected by turns, the turns comprising alternating peaks and valleys. Each second serpentine band includes a plurality of bent struts connected by turns, the turns comprising alternating peaks and valleys. The stent further comprising a plurality of connector struts, wherein adjacent serpentine bands are connected by at least one connector strut. Each connector strut extends from a valley of one serpentine band to a peak of another serpentine band. The first and second serpentine bands alternate along the length of the stent.

In at least one other embodiment, a stent comprises a plurality serpentine bands, each serpentine band comprising a plurality of struts connected by turns, the turns comprising alternating peaks and valleys. The serpentine bands include a plurality of first serpentine bands, each first serpentine band comprising a plurality of straight struts connected by alternating peaks and valleys. At least one first serpentine band includes a first peak, a plurality of second peaks, a first valley and a plurality of second valleys. The second peaks are aligned about a circumference of a stent and the first peak is longitudinally offset from the second peaks. The second valleys are aligned about a circumference of a stent, and the first valley is longitudinally offset from the second valleys. The serpentine bands further including a plurality of second serpentine bands, each second serpentine band comprising a plurality of bent struts connected by alternating peaks and valleys. A plurality of second serpentine bands comprise a first peak, a plurality of second peaks, a first valley and a plurality of second valleys. The second peaks are aligned about a circumference of a stent, and the first peak is longitudinally offset from the second peaks. The second valleys are aligned about a circumference of a stent, and the first valley is longitudinally offset from the second valleys. Longitudinally adjacent serpentine bands are connected by a connection, a connection comprising a first valley that is connected to a first peak.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.
FIGS. 1-31 show various embodiments of stent patterns.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

Depicted in the figures are various aspects of the invention. Elements depicted in one figure may be combined with, and/or substituted for, elements depicted in another figure as desired. For the purposes of this disclosure, like reference numerals in the Figures shall refer to like features unless otherwise indicated.

FIGS. 1-12 show various embodiments of patterns for a stent 10. Each embodiment of a stent 10 has a proximal end 12 a distal end 14, and includes a plurality of serpentine bands 20. Each serpentine band 20 includes a plurality of struts 22, each strut 22 having a first end 21 and a second end 23. Circumferentially adjacent struts 22 within a serpentine band 20 are connected by turns 28. Turns 28 located on a proximal side of a serpentine band 20 comprise proximal peaks 24, and turns 28 located on a distal side of a serpentine band 20 comprise distal troughs or valleys 26.

Serpentine bands 20 which are adjacent to one another along the length of the stent 10 are connected by at least one connector strut 16. In some embodiments, a connector strut 16 may span between turns 28 of adjacent serpentine bands 20. For example, a first end 17 of a connector strut 16 may connect to a distal valley 26 of one serpentine band 20, and a second end 18 of the connector strut 16 may connect to a proximal peak 24 of an adjacent serpentine band 20.

The struts 22 of a serpentine band 20 may comprise straight struts 30 and/or bent struts 32. A straight or linear strut 30 is substantially straight along its length. A bent strut 32 desirably includes curvature along its length. In some embodiments, a bent strut 32 may comprise an s-shape. In some embodiments, an s-shape may comprise a first curved portion 34 and a second curved portion 35. The curvature orientation of the first curved portion 34 may be different than the curvature orientation of the second curved portion 35. For example, if the first curved portion 34 may be considered convex, the second curved portion 35 may be considered concave. An s-shaped strut 32 may include an inflection point 33 where the curvature changes orientation. In some embodiments, an s-shape may comprise a first portion 46, a second portion 47 and a third portion 48. The first portion 46 and the third portion 48 may be parallel or substantially parallel to one another, and may extend at an angle to the stent lengthwise axis 11. The second portion 47 may be centrally located between the first portion 46 and the third portion 48, and may extend an angle to the stent lengthwise axis 11 different the first portion 46 or the third portion 48. In some embodiments, an angle between the stent lengthwise axis 11 and the first portion 46 may comprise a mirror image of an angle between the stent lengthwise axis 11 and the second portion 47, the mirror image taken across a stent circumferential line.

In some embodiments, a serpentine band 20 may comprise alternating straight struts 30 and bent or s-shaped struts 32. Each straight strut 30 may be oriented between two bent struts 32. Thus, a first end 21 of a straight strut 30 may be connected to a proximal peak 24 which may connect to a bent strut 32 located on one side of the straight strut 30. A second end 23 of the straight strut 30 may be connected to a distal valley 26 which may connect to another bent strut 32 located on the other side of the straight strut 30. Similarly, each bent strut 32 may be oriented between two straight struts 30. Thus, a first end 21 of a bent strut 32 may be connected to a proximal peak 24 which may connect to a straight strut 30 located on one side of the bent strut 32. A second end 23 of the bent strut 32 may be connected to a distal valley 26 which may connect to another straight strut 30 located on the other side of the bent strut 32.

Each strut 22 has a width. In some embodiments, all struts 22 may have the same width. In some embodiments, bent struts 32 may have a different width that straight struts 30. In various other embodiments, individual struts 22 may each have any suitable width dimension.

Each turn 28 has a width. In some embodiments, the width of a turn 28 may be greater than the width of one or more struts 22 of the stent 10. In some embodiments, the width of a turn 28 may be less than the width of one or more struts 22 of the stent 10. In some embodiments, the width of a turn 28 may vary from one end of the turn to the other. For example, a turn 28 may connect to a straight strut 30 at one end having the same width as the straight strut 30. The width of the turn 28 may increase, and in some embodiments may reach a maximum at a midpoint of the turn. The width of the turn 28 may then decrease to the width of a bent strut 32, which may be connected to the second end of the turn 28.

Connector struts 16 span between adjacent serpentine bands 20. Connector struts 16 may connect to any portion of a serpentine band 20, such as a turn 28, or in some embodiments, a strut 22. In some embodiments, a connector strut 16 may be linear or straight along its length.

In some embodiments, a stent 10 may comprise a first type of connector strut 36 and a second type of connector strut 38. A first connector strut 36 may extend in a first direction. The first connector strut 36 may be oriented at a first angle to a stent lengthwise axis 11. A second connector strut 38 may extend in a second direction that is different than or non-parallel to the first direction. Therefore, a second connector strut 38 may be oriented at a second angle to a stent lengthwise axis 11, the second angle being different than the first angle. In some embodiments, the first angle and the second angle may have the same magnitude but different orientations. For example, a first connector strut 36 may form a 70° angle with a stent lengthwise axis 11, while a second connector strut 38 may form a negative 70° angle with the stent lengthwise axis 11. In some embodiments, a first angle may comprise a mirror image of a second angle across a line parallel to the stent lengthwise axis 11.

In some embodiments, all of the first connector struts 36 of the stent 10 may be parallel to one another. In some embodiments, a first connector strut 36 may extend between turns 28 which connect a straight strut 30 to a bent strut 32. In some embodiments, each side of the first connector strut 36 may extend from a turn 28 in the direction of the side of the turn 28 which connects to a bent strut 32.

In some embodiments, all of the second connector struts 38 of the stent 10 may be parallel to one another. In some embodiments, a second connector strut 38 may extend between turns 28 which connect a straight strut 30 to a bent strut 32. In some embodiments, each side of the second connector strut 38 may extend from a turn 28 in the direction of the side of the turn 28 which connects to a straight strut 30.

Each serpentine band 20 may include unconnected turns 29 from which no connector strut 16 extends.

Figure 4:
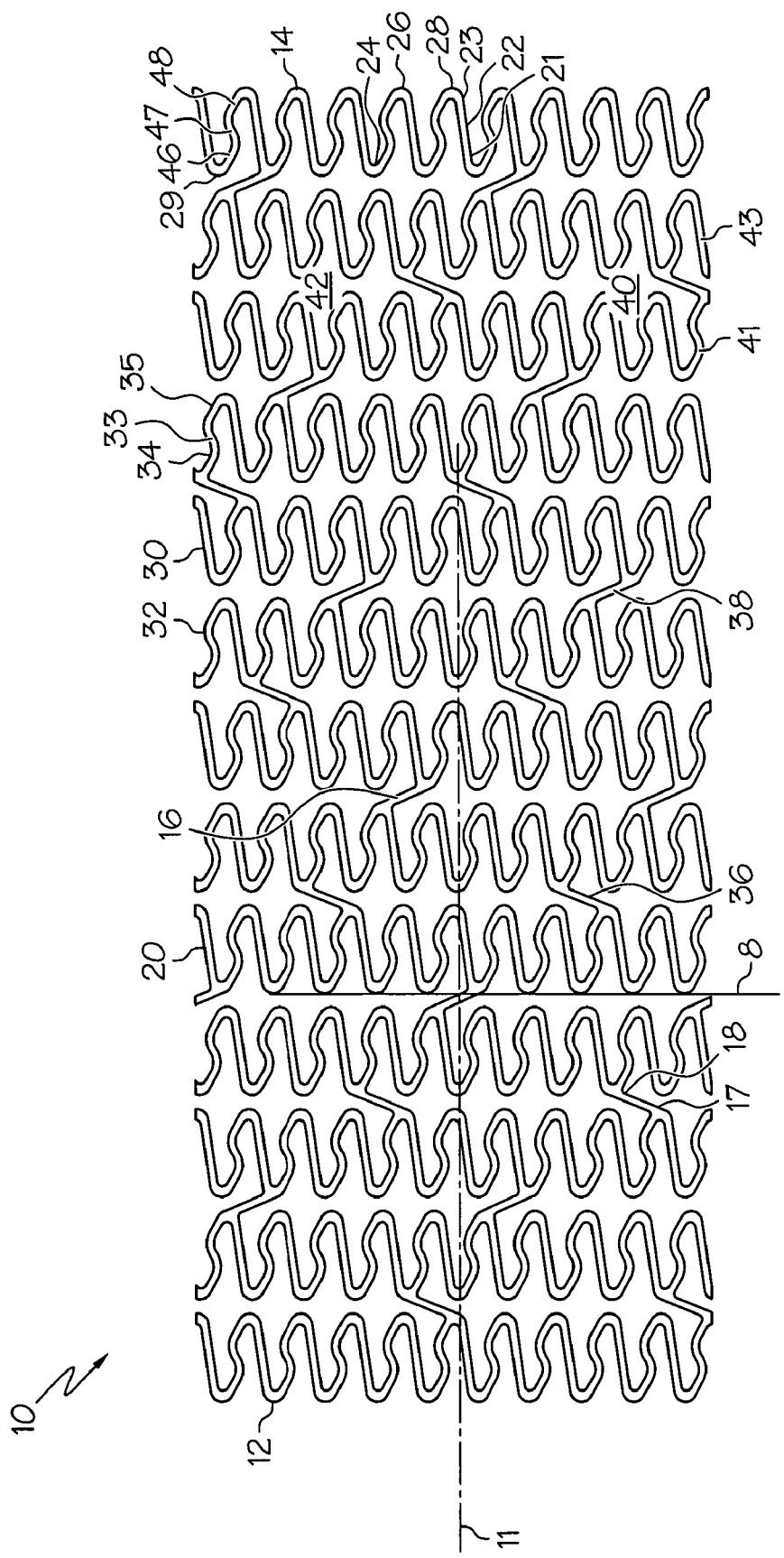
Figure 5:
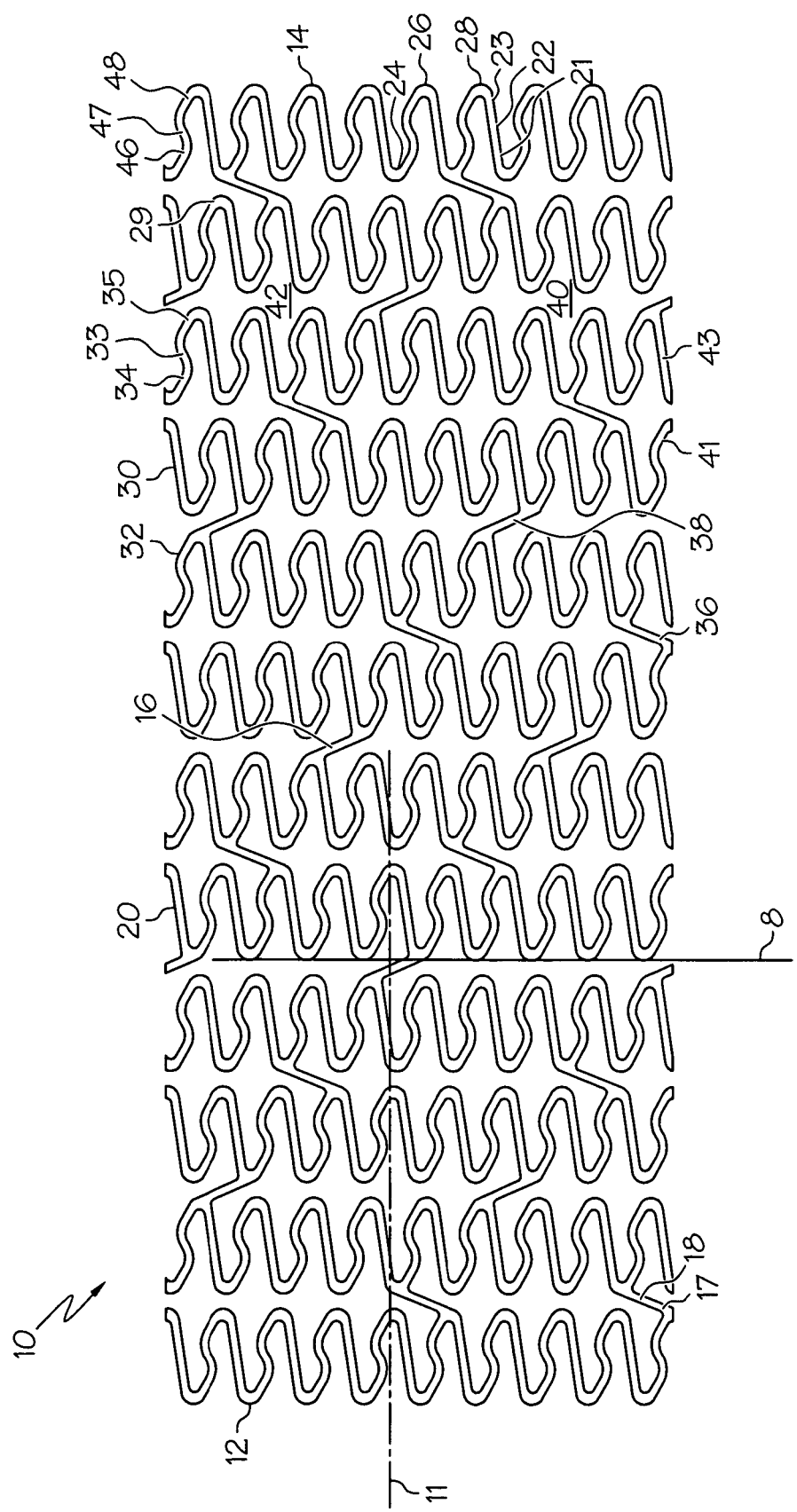
Figure 6:
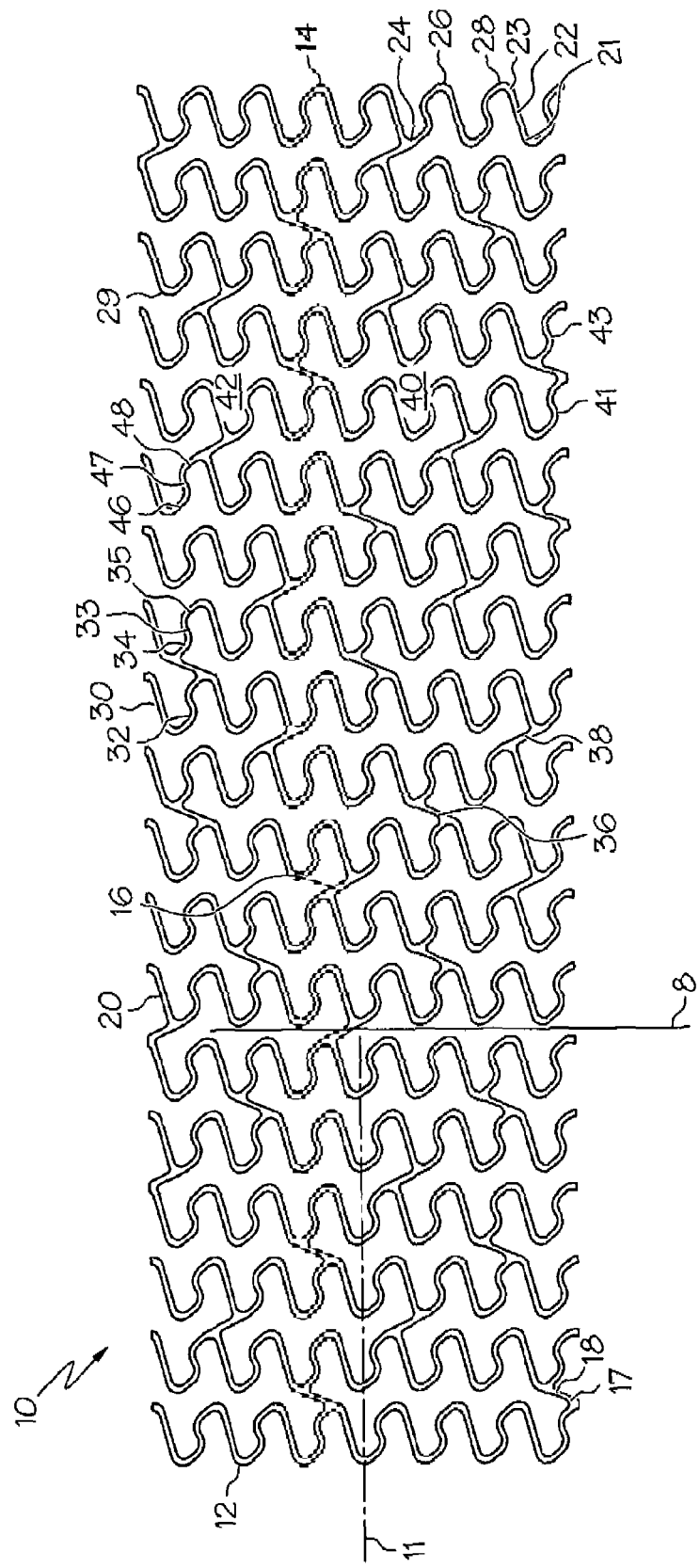
Figure 7:
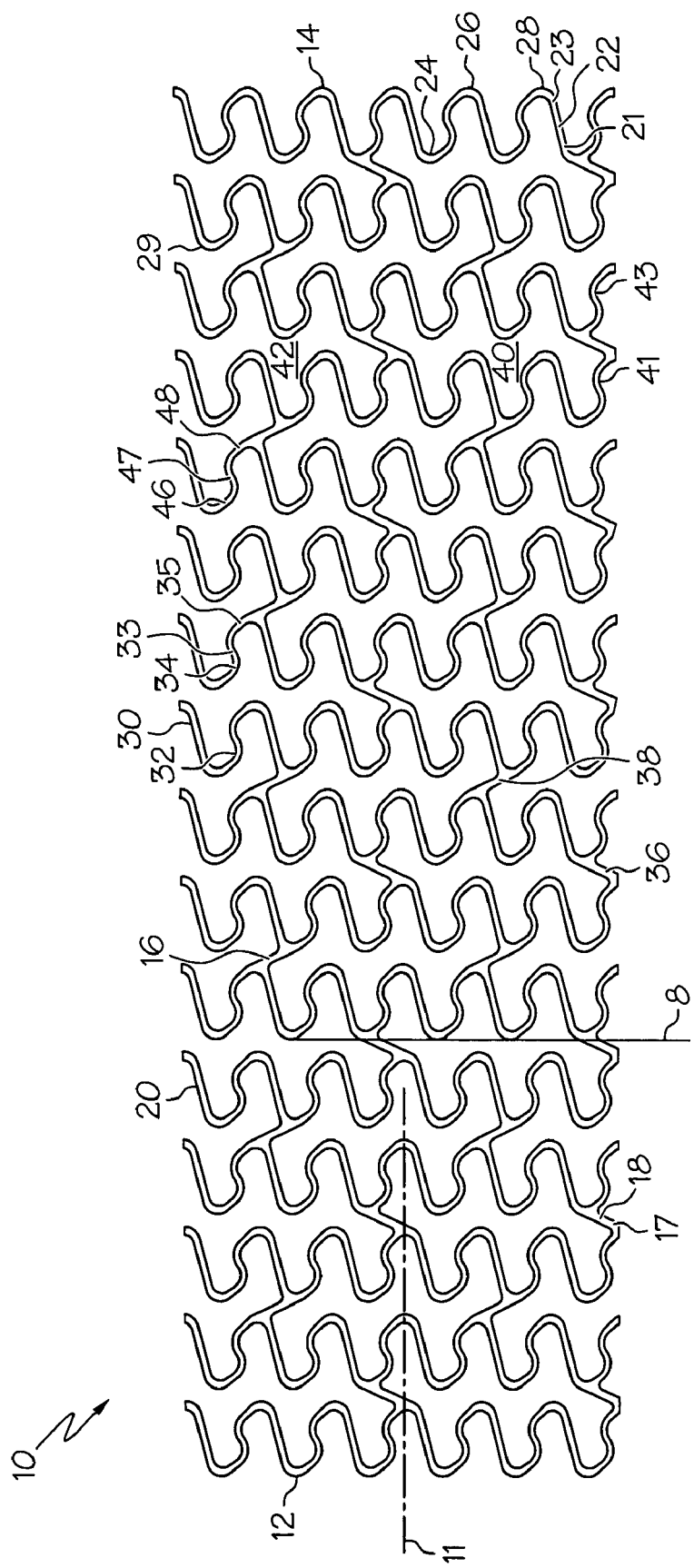
Figure 8:
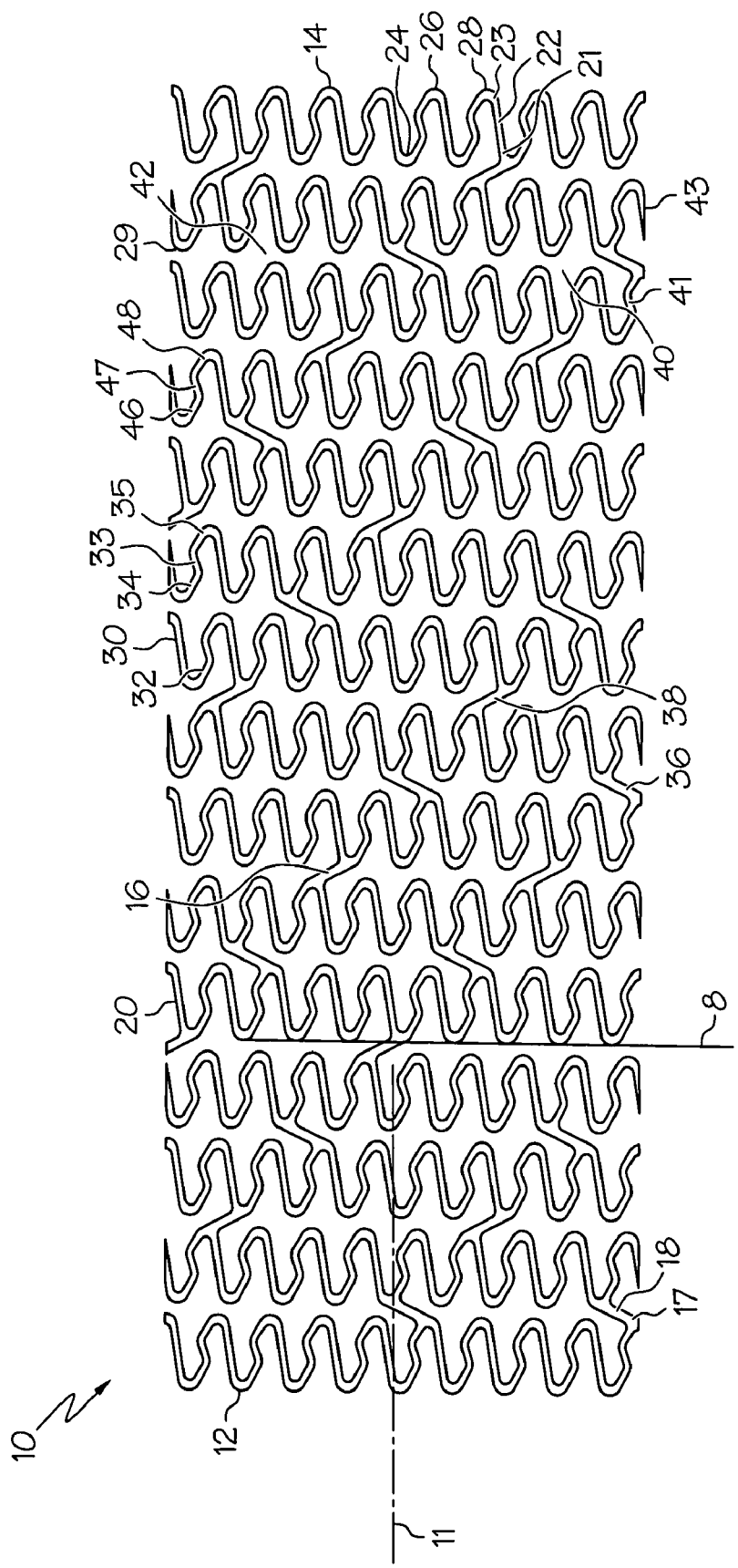
Figure 9:
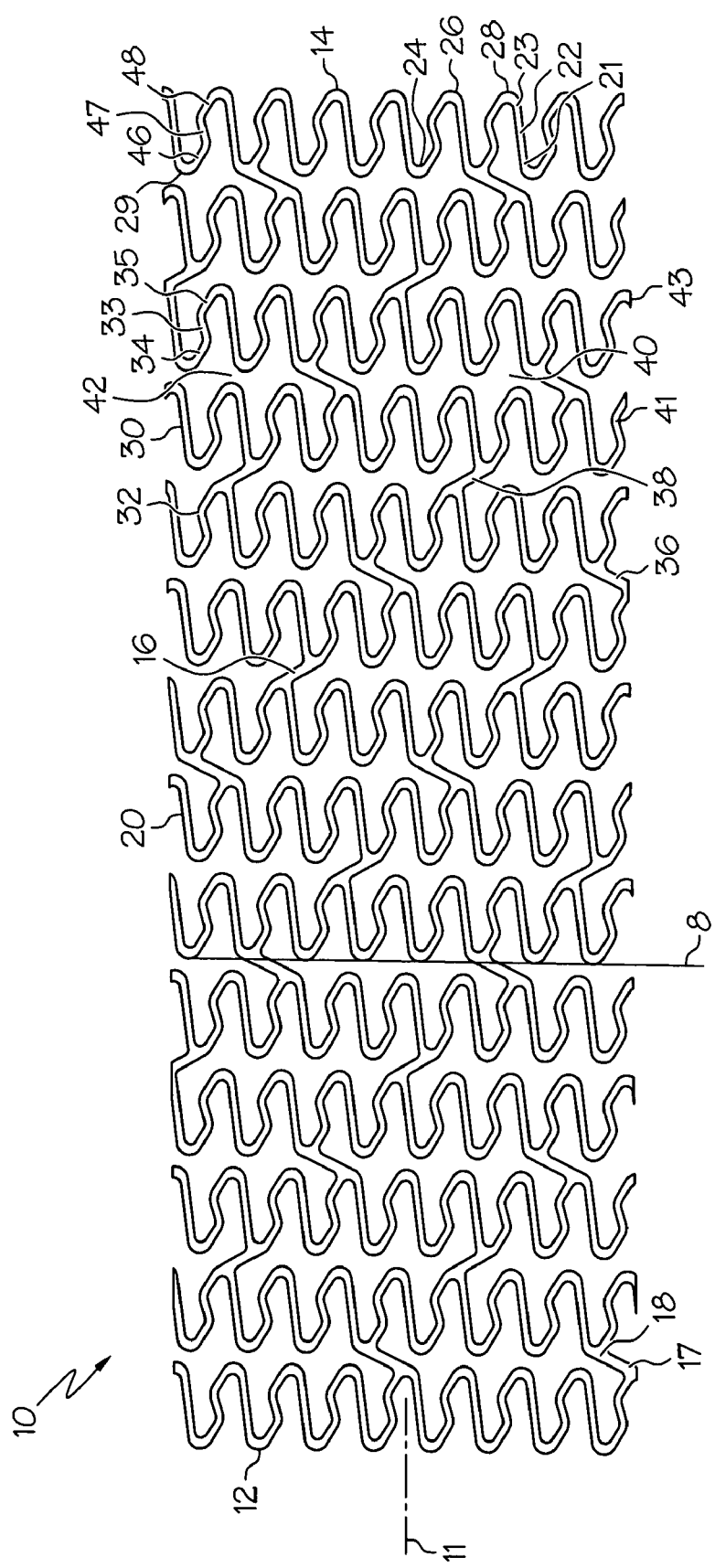
Figure 10:
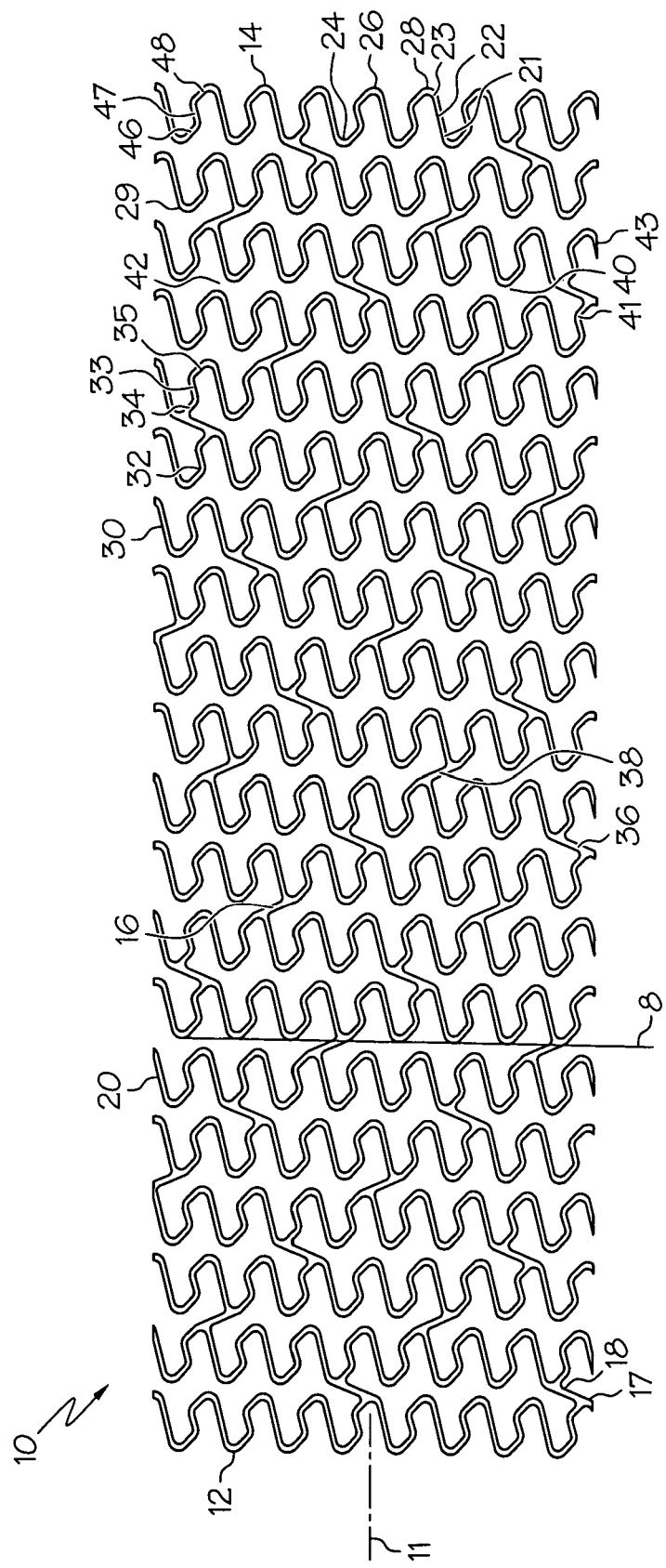
Figure 11:
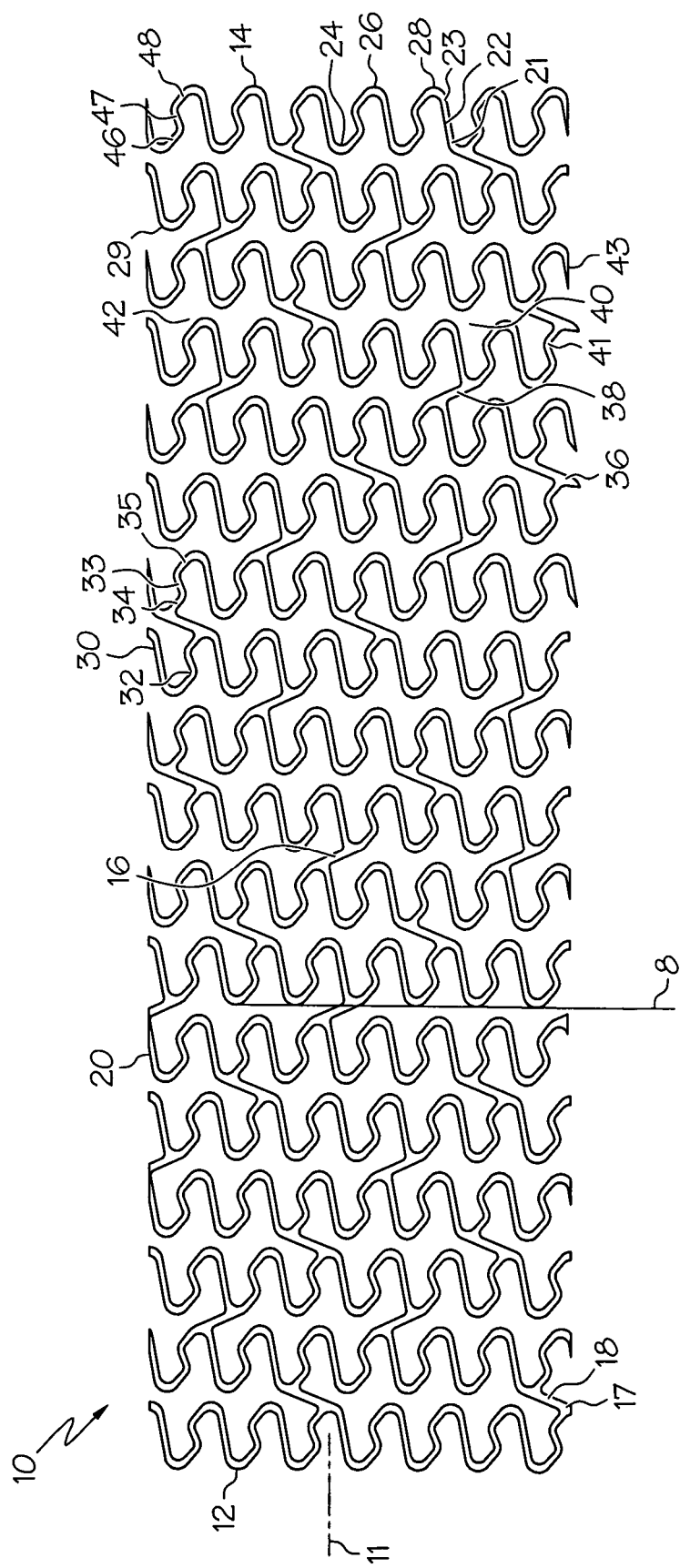

A stent 10 may have any suitable number of serpentine bands 20. In some embodiments, a stent 10 may comprise an even number of serpentine bands 20. In some embodiments, for example as shown in FIGS. 4, 6, and 8, a stent 10 may comprise an odd number of serpentine bands 20.

A stent 10 may have any suitable number of struts 22 per serpentine band 20. A stent 10 may further have any suitable number of connector struts 16 extending between adjacent serpentine bands 20.

A stent 10 may comprise a plurality of cells 40. A cell 40 may comprise an opening in the stent 10 wall portion between serpentine bands 20 and connector struts 16. In some embodiments, a cell 40 may be bounded by a serpentine band 20, a connector strut 16, another serpentine band 20 and another connector strut 16.

In some embodiments, for example as shown in FIGS. 1-4, 7, 9 and 10, a serpentine band 20 includes an even number of proximal peaks 24 and an even number of distal valleys 26. The stent 10 further comprises an even number of connector struts 16 extending between adjacent serpentine bands 20. When the connector struts 16 are evenly distributed between the turns 28 of the adjacent serpentine bands 20, the cells 40 oriented between the adjacent serpentine bands 20 are similar in size and shape. Connector struts 16 may be considered evenly distributed between the turns 28 of adjacent serpentine bands 20 if an equal number of unconnected turns 29 are oriented between the adjacent connector struts 16. For example, a stent 10 may include a serpentine band 41 and an adjacent serpentine band 43. In some embodiments, two connector struts 16 may extend between the adjacent serpentine bands 41, 43. Two cells 40, 42 may be oriented between the adjacent serpentine bands 41, 43. The number of unconnected turns 29 of serpentine band 41 bounding cell 40 is equal to the number of unconnected turns 29 of serpentine band 41 bounding cell 42. The cells 40, 42 may be similar in size and shape.

In some embodiments, for example as shown in FIGS. 5, 6, 8, 11 and 12, a serpentine band 20 includes an odd number of proximal peaks 24 and an odd number of distal valleys 26. The stent 10 further comprises an even number of connector struts 16 extending between adjacent serpentine bands 20. The odd number of turns 28 of a serpentine band and the even number of connector struts 16 may lead to connector struts 16 that are not evenly distributed between the turns 28 of the adjacent serpentine bands 20. The cells 40 oriented between the adjacent serpentine bands 20 may be different in size and shape. For example, a stent 10 may include a serpentine band 41 and an adjacent serpentine band 43. Two connector struts 16 may extend between the adjacent serpentine bands 41, 43. Two cells 40, 44 may be oriented between the adjacent serpentine bands 41, 43. The number of unconnected turns 29 of serpentine band 41 bounding cell 40 is not equal to the number of unconnected turns 29 of serpentine band 41 bounding cell 44. The cells 40, 44 may be different in size and shape.

In some embodiments, for example as shown in FIGS. 1 and 4-12, the proximal peaks 24 of a serpentine band 20 are circumferentially aligned, and the distal valleys 26 of a serpentine band 20 are circumferentially aligned. For example, a reference line 8 oriented about a circumference of the stent 10 which contacts the outer proximal side of a proximal peak 24 of a serpentine band 20 may contact the outer proximal side of all of the proximal peaks 24 of the serpentine band 20. In some embodiments, the distal valleys 26 of serpentine bands 20 may be similarly aligned.

Figure 2:
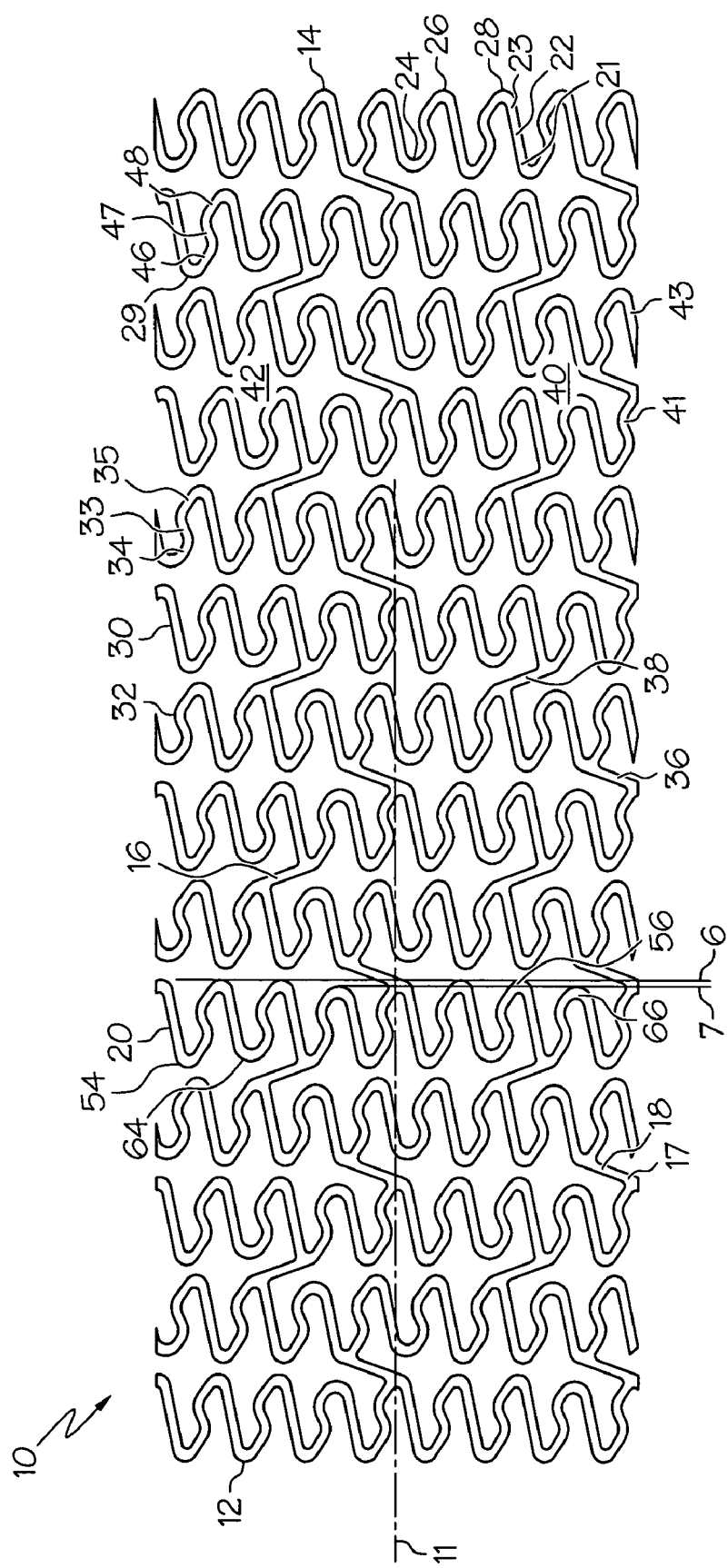
Figure 3:
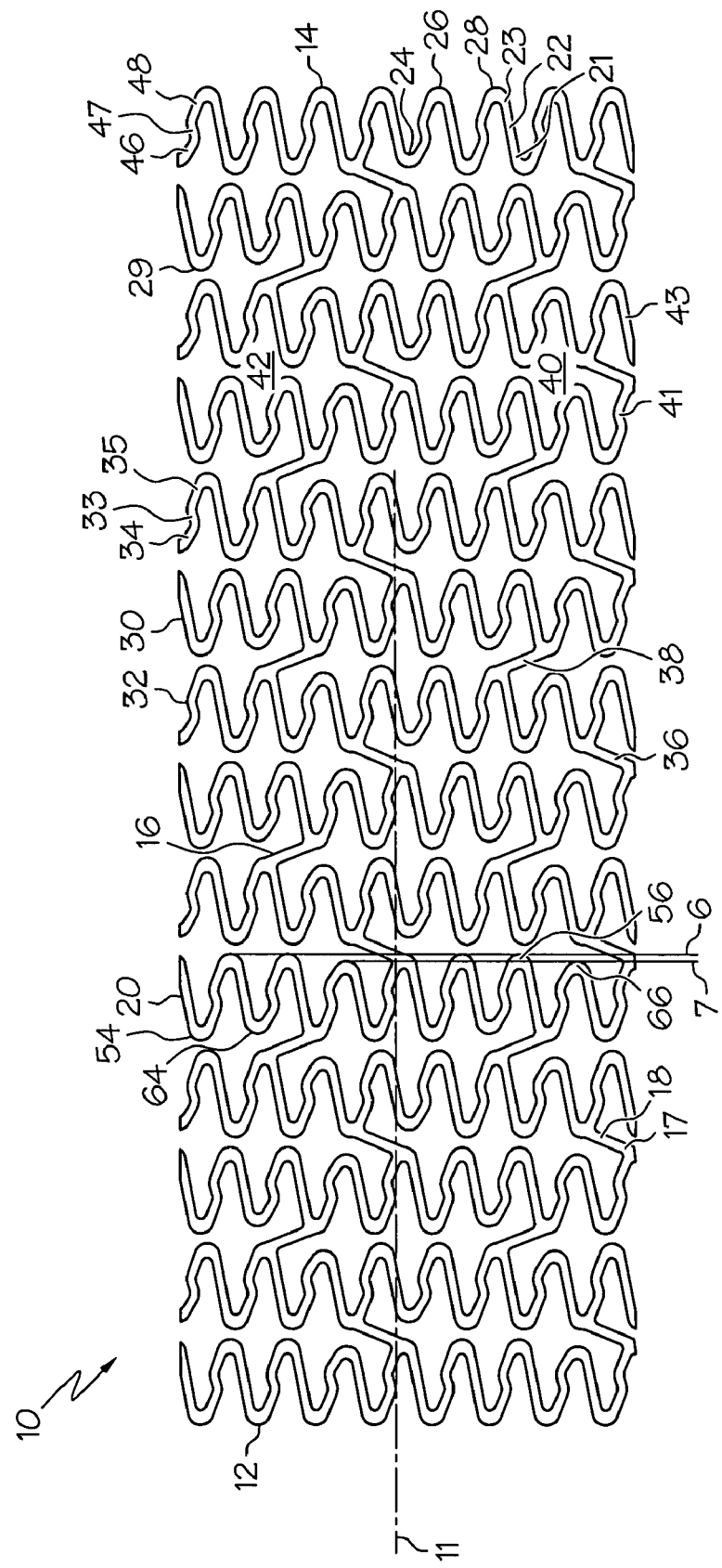

In some embodiments, for example as shown in FIGS. 2 and 3, a portion of the proximal peaks 24 of a serpentine band 20 are longitudinally offset from other proximal peaks 24 of the band 20. Similarly, in some embodiments, a portion of the distal valleys 26 of a serpentine band 20 are longitudinally offset from other distal valleys 26 of the band 20. For example, a first reference line 6 may be oriented about a circumference of the stent 10 and may contact the outer distal side of a portion of the distal valleys 26 of a serpentine band 20. A second reference line 7 may be oriented about a circumference of the stent 10, may be offset from the first reference line 6, and may contact the outer distal side of at least a portion of distal valleys 26 of the serpentine band 20 that do not contact the first reference line 6. In some embodiments, each distal turn 26 of the serpentine band 20 may contact either the first reference line 6 or the second reference line 7.

In some embodiments, the proximal turns 24 of a serpentine band 20 may comprise first proximal turns 54 and second proximal turns 64. The distal turns 26 of a serpentine band 20 may comprise first distal turns 56 and second distal turns 66. The first distal turns 56 of a serpentine band 20 may extend farther toward the distal end 14 of the stent 10 than the second distal turns 66. The first distal turns 56 of a serpentine band 20 may all be circumferentially aligned with one another, for example all contacting the first reference line 6. The second distal turns 66 of a serpentine band 20 may all be circumferentially aligned with one another, for example all contacting the second reference line 7. Similarly, the first proximal turns 54 of a serpentine band 20 may extend farther toward the proximal end 12 of the stent 10 than the second proximal turns 64. The first proximal turns 54 of a serpentine band 20 may all be circumferentially aligned with one another, and the second proximal turns 64 of a serpentine band 20 may all be circumferentially aligned with one another.

In some embodiments, each connector strut 16 may span from a first distal turn 56 to a first proximal turn 54.

In some embodiments, a second proximal turn 64 may be located across a cell 40 from a turn 28 of another serpentine band 20 that connects to a connector strut 16. A second distal turn 66 may be located across a cell 40 from a turn 28 of another serpentine band 20 that connects to a connector strut 16. Thus, the amplitude of a serpentine band 20 waveform may be less in areas that are adjacent to connector struts 16 along the length of the stent 10. This configuration of spacing between various turns 28 and connector struts 16 desirably results in better stent crimpability.

In some embodiments, the various struts 22 of a serpentine band 20 may have different lengths. In some embodiments, the various struts 22 of a serpentine band 20 may have different longitudinal length components as measured in a direction parallel to the stent lengthwise axis 11 between the first end 21 and the second end 23 of the strut 22. Struts 22 that connect between a first proximal turn 54 and a first distal turn 56 may have a first longitudinal length component. Struts 22 that connect between a first proximal turn 54 and a second distal turn 66, and struts 22 that connect between a second proximal turn 64 and a first distal turn 64, may have a second longitudinal length component. The second longitudinal length component may be less than the first longitudinal length component. Struts 22 that connect between a second proximal turn 64 and a second distal turn 66 may have a third longitudinal length component. The third longitudinal length component may be less than the second longitudinal length component.

Figure 12:
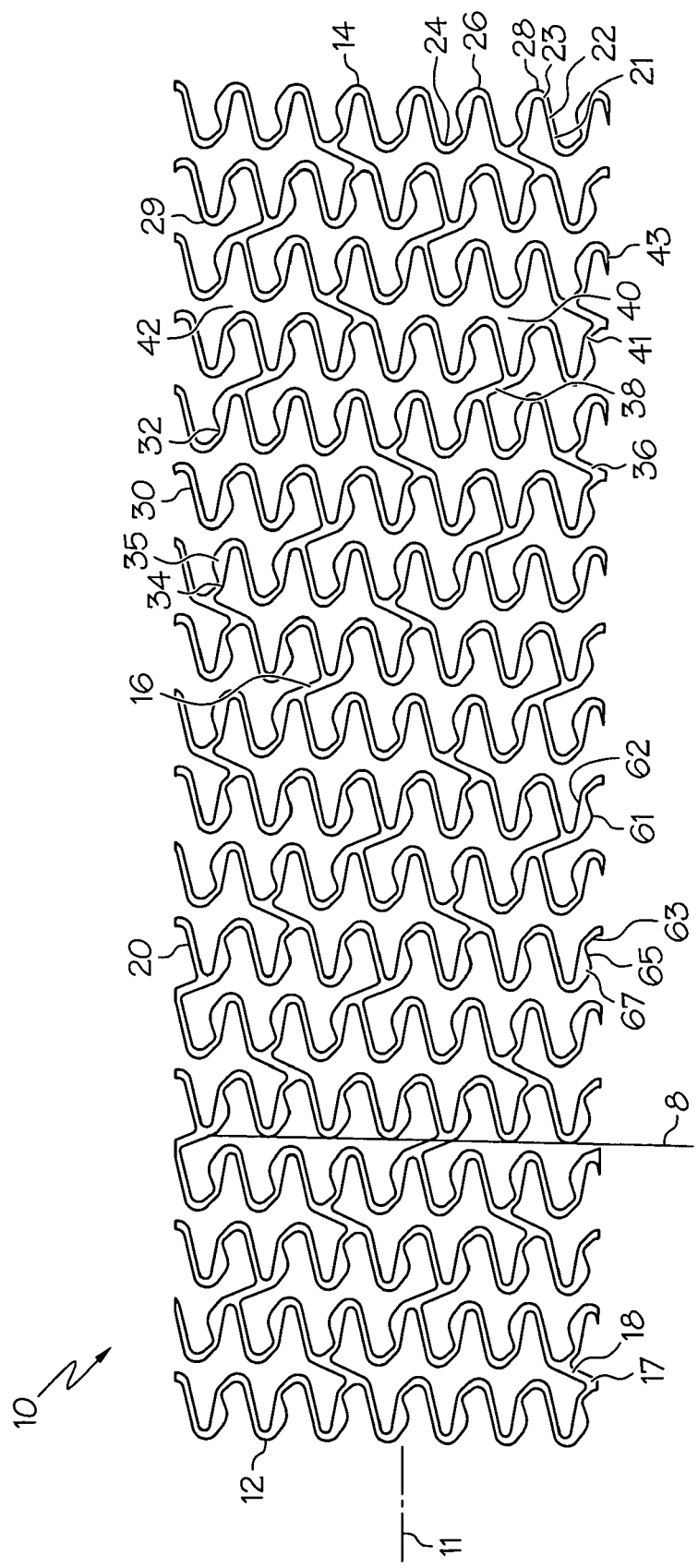

FIG. 12 shows an embodiment of a pattern for a stent 10 wherein the s-shaped struts 32 include a first side wall 61 and a second side wall 62. A side wall 61, 62 is desirably oriented in a stent radial direction. The first side wall 61 comprises an s-shape. The second side wall 62 comprises a shape that is different than the first side wall 61. In some embodiments, the second side wall 62 may be straight. Each s-shaped 32 strut may vary in width, and may comprise a first portion 63 and a second portion 65. The first portion 63 may have a first width that may be equal to the width of a straight strut 30. The second portion 65 may have a varying width that may be larger than the width of the first portion 63. The second portion 65 may comprise a lobe 67 of an s-shaped strut 32.

Figure 13:
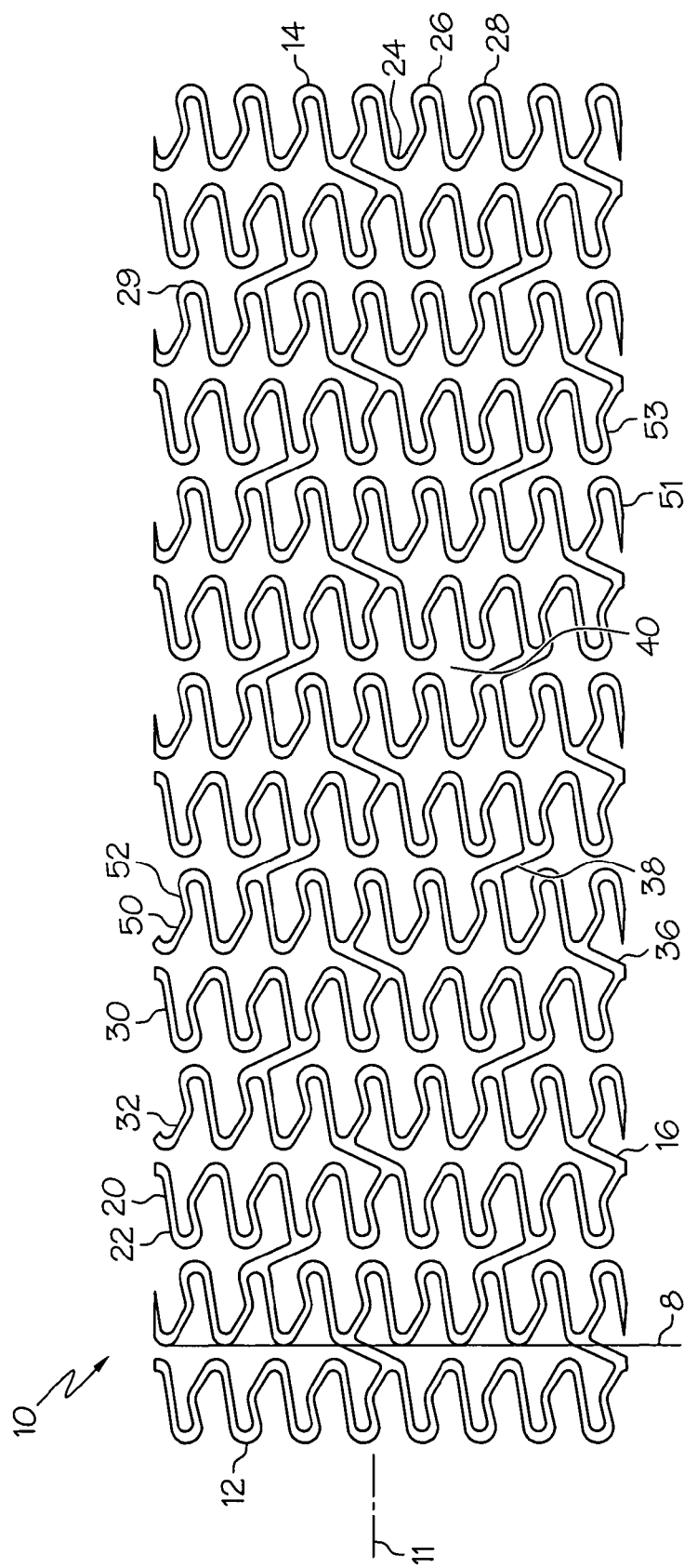

FIG. 13 shows another embodiment of a pattern for a stent 10 which comprises serpentine bands 20 connected by connector struts 16. Bent struts 32 of a serpentine band 20 include a first portion 50 and a second portion 52. The first portion 50 extends at an angle to the stent lengthwise axis 11, and the second portion 52 extends at another angle to the stent lengthwise axis 11.

The serpentine bands 20 further comprise first serpentine bands 51 and second serpentine bands 53. Bent struts 32 included in first serpentine bands 51 have curvature of a first orientation. Bent struts 32 included in the second serpentine bands 53 have curvature of a second orientation that is different than first orientation. For example, from a given reference point, if the bent struts 32 included in a first serpentine band 51 may be considered convex, the bent struts 32 included in a second serpentine band 53 may be considered concave.

Figure 14:
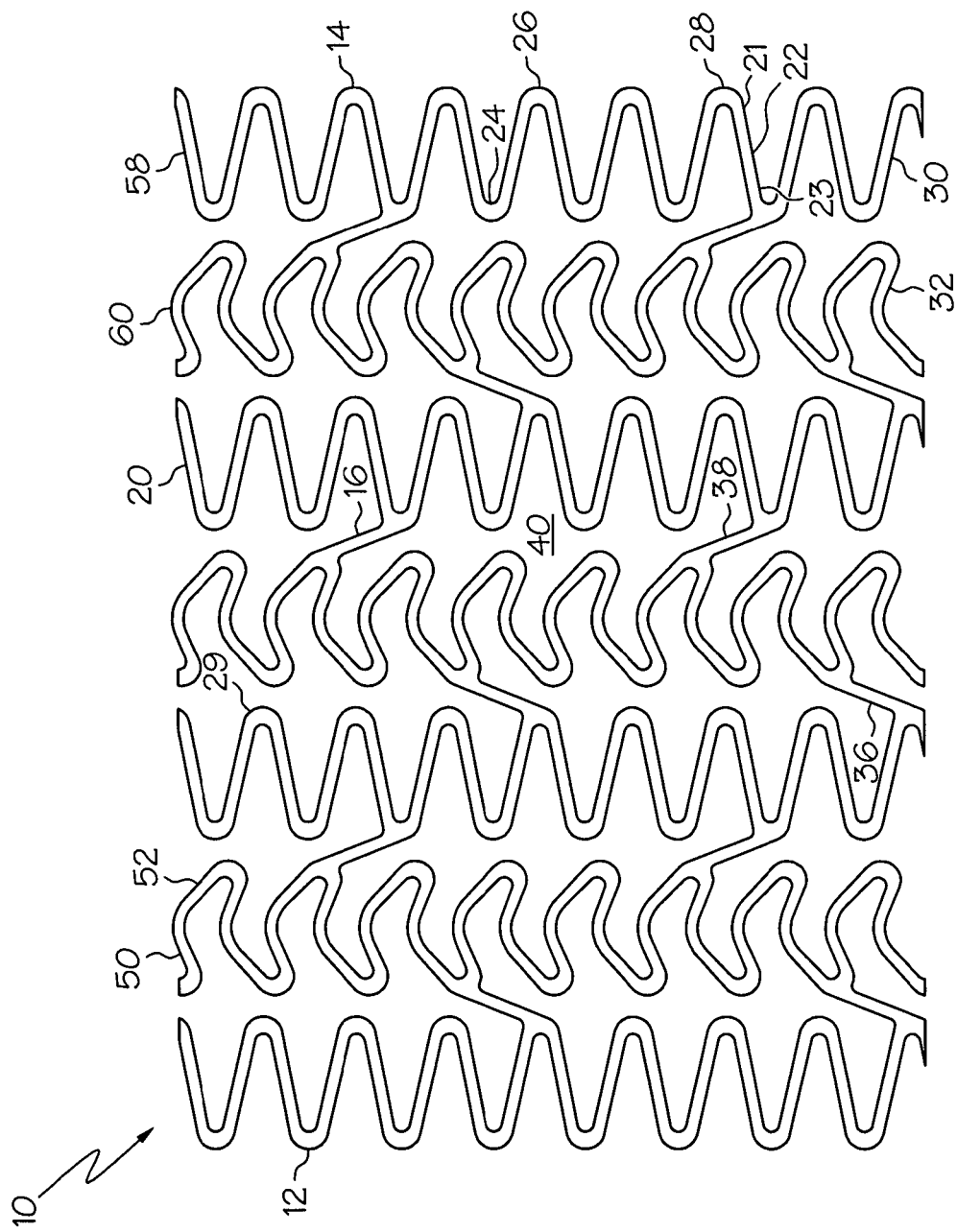

FIG. 14 shows another embodiment of a pattern for a stent 10 comprising serpentine bands 20 connected by connector struts 16. As previously mentioned, like reference numerals in the Figures shall refer to like features as described herein. Serpentine bands comprise first serpentine bands 58 and second serpentine bands 60. The first serpentine bands 58 and second serpentine bands 60 may alternate along the length of the stent 10.

The first serpentine bands 58 comprise straight struts 30 connected by turns 28. The second serpentine bands 60 comprise bent struts 32 connected by turns. Each turn 28 may have a width, and the width of a turn 28 may be greater than the width of one or more struts 22 of the stent 10. The width of a turn 28 may increase from a strut 22 width at its ends and reach a maximum at a midpoint of the turn 28. In some embodiments, the width of a turn 28 may be less than the width of one or more struts 22 of the stent 10, and the width of a turn 28 may decrease from a strut 22 width at its ends and reach a minimum at a midpoint of the turn 28.

Connector struts 16 comprise a first type of connector strut 36 and a second type of connector strut 38. A first connector strut 36 extends in a first direction which may be oriented at a first angle to a stent lengthwise axis 11. A second connector strut 38 extends in a second direction that is different than or non-parallel to the first direction.

First connector struts 36 extend from a distal valley 26 of a first serpentine band 58 to a proximal peak 24 of a second serpentine band 60. Second connector struts 38 extend from a distal valley 26 of a second serpentine band 60 to a proximal peak 24 of a first serpentine band 58.

Figure 15:
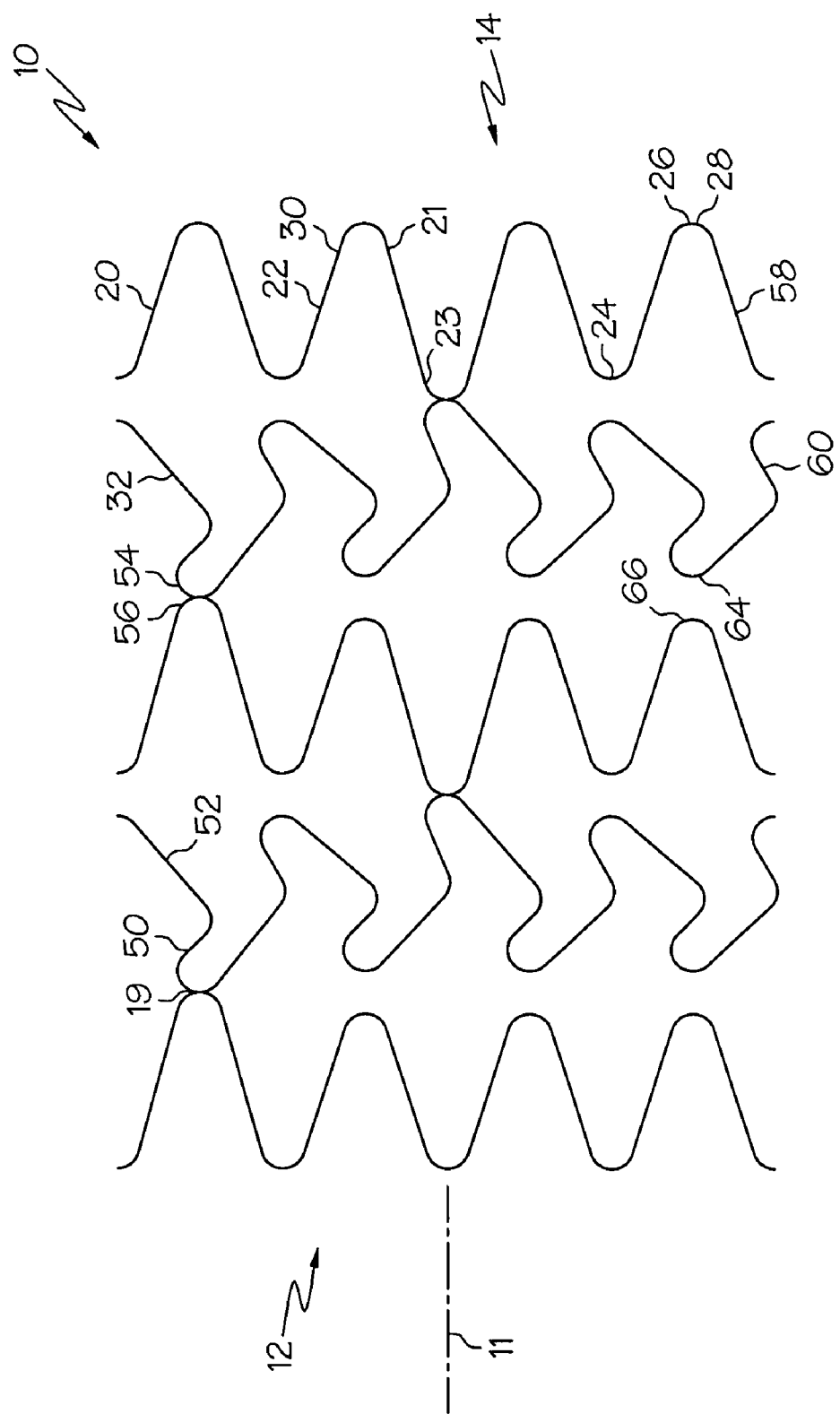

FIG. 15 shows another embodiment of a pattern for a stent 10 comprising first serpentine bands 58 and second serpentine bands 60. The proximal turns 24 of a serpentine band 20 comprise first proximal turns 54 and second proximal turns 64. The distal turns 26 of a serpentine band 20 comprise first distal turns 56 and second distal turns 66. The first distal turns 56 of a serpentine band 20 extend farther toward the distal end 14 of the stent 10 than the second distal turns 66. The second distal turns 66 of a serpentine band 20 are all circumferentially aligned with one another. Similarly, the first proximal turns 54 of a serpentine band 20 extend farther toward the proximal end 12 of the stent 10 than the second proximal turns 64. The second proximal turns 64 of a serpentine band 20 are all circumferentially aligned with one another.

Various struts 22 of a serpentine band 20 may have different longitudinal length components as measured in a direction parallel to the stent lengthwise axis 11 between the first end 21 and the second end 23 of the strut 22. Struts 22 that connect to a first proximal turn 54 or to a first distal turn 56 may have a first longitudinal length component. Struts 22 that connect between a second proximal turn 64 and a second distal turn 66 may have a second longitudinal length component. The second longitudinal length component may be less than the first longitudinal length component.

Adjacent serpentine bands 20 may be connected by at least one connection 19. Connections 19 may comprise a first distal turn 56 that is attached to a first proximal turn 54.

Figure 16:
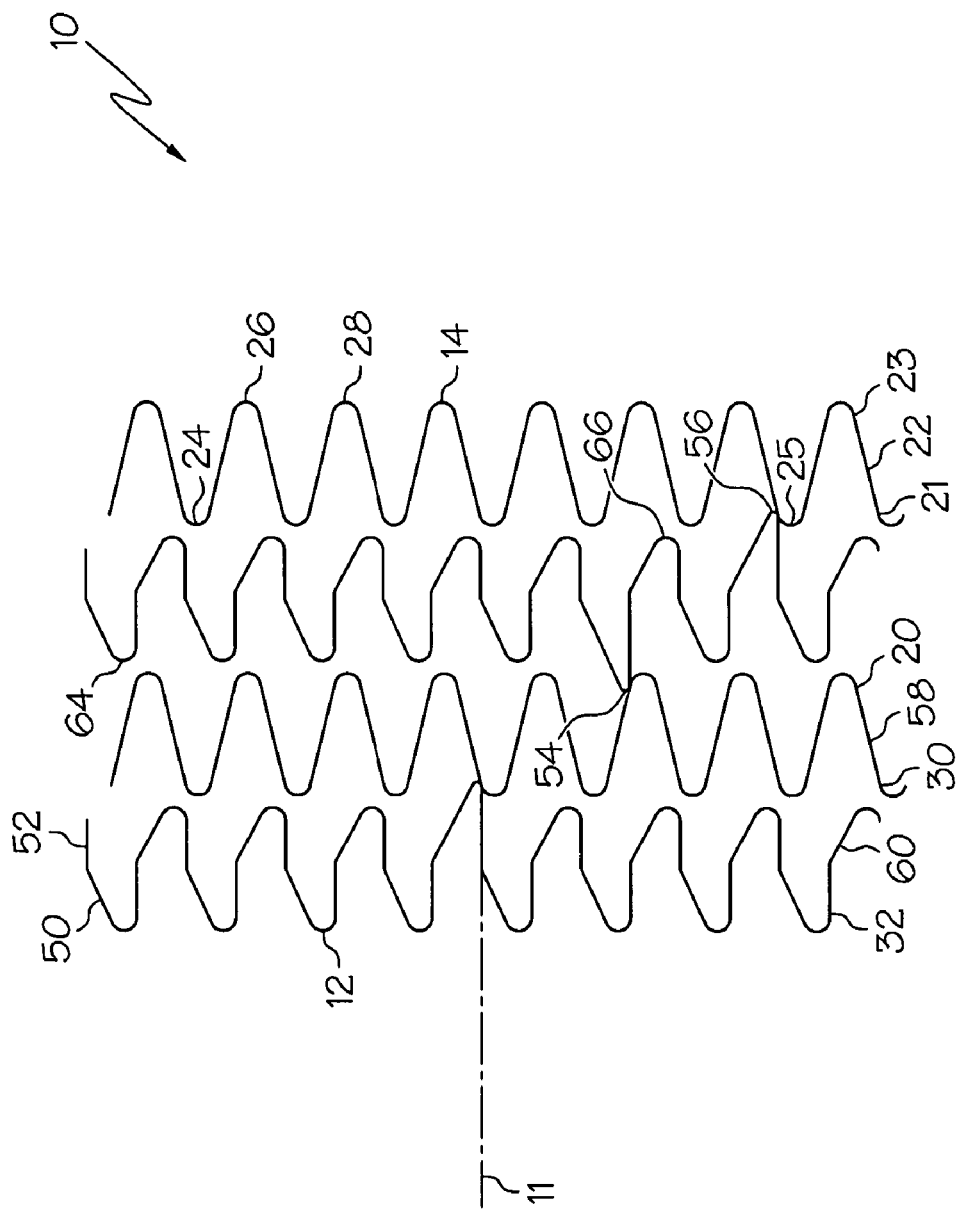

FIG. 16 shows another embodiment of a pattern for a stent 10 comprising first serpentine bands 58 and second serpentine bands 60. Second serpentine bands 60 comprise bent struts 32 connected by turns 28. The proximal turns 24 of a second serpentine band 60 comprise first proximal turns 54 and second proximal turns 64. The distal turns 26 of a second serpentine band 60 comprise first distal turns 56 and second distal turns 66. The first distal turns 56 extend farther toward the distal end 14 of the stent 10 than the second distal turns 66. The second distal turns 66 are all circumferentially aligned with one another. Similarly, the first proximal turns 54 extend farther toward the proximal end 12 of the stent 10 than the second proximal turns 64. The second proximal turns 64 are all circumferentially aligned with one another.

Various struts 22 of a second serpentine band 60 may have different longitudinal length components as measured in a direction parallel to the stent lengthwise axis 11 between the first end 21 and the second end 23 of the strut 22. Struts 22 that connect to a first proximal turn 54 or to a first distal turn 56 may have a first longitudinal length component. Struts 22 that connect between a second proximal turn 64 and a second distal turn 66 may have a second longitudinal length component. The second longitudinal length component may be less than the first longitudinal length component.

Adjacent serpentine bands 20 are connected by at least one connection 25. Connections 25 comprise a first proximal turn 54 or a first distal turn 56 that is attached to any portion of an adjacent serpentine band 20.

Figure 17:
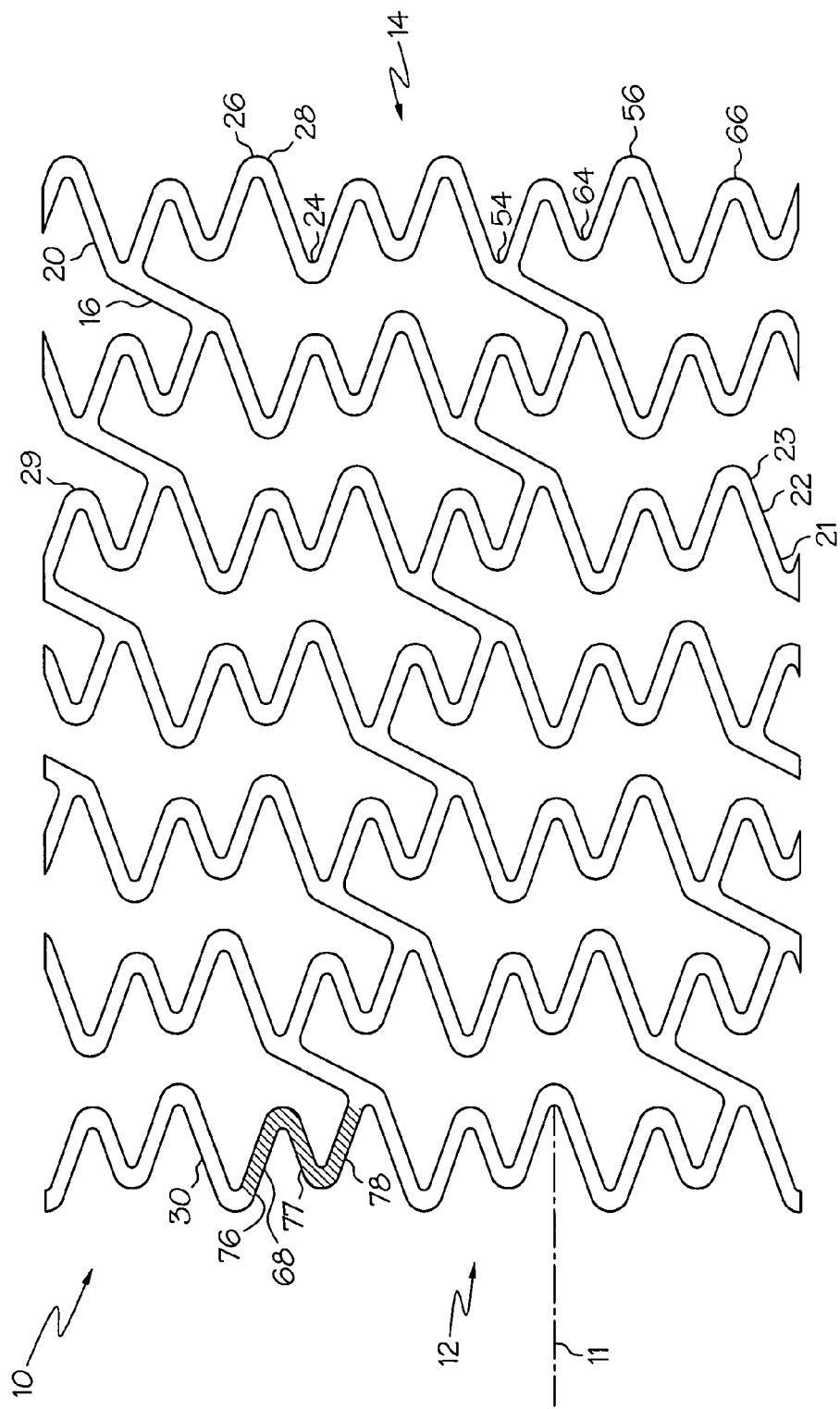

FIG. 17 shows another embodiment of a pattern for a stent 10 comprising serpentine bands 20 connected by connector struts 16. A serpentine band 20 includes proximal turns 24 and distal turns 26. The proximal turns 24 may comprise first proximal turns 54 and second proximal turns 64. The distal turns 26 of a serpentine band 20 may comprise first distal turns 56 and second distal turns 66. The first distal turns 56 of a serpentine band 20 extend farther toward the distal end 14 of the stent 10 than the second distal turns 66. The first distal turns 56 of a serpentine band 20 are all circumferentially aligned with one another, and the second distal turns 66 of a serpentine band 20 are all circumferentially aligned with one another. Similarly, the first proximal turns 54 of a serpentine band 20 extend farther toward the proximal end 12 of the stent 10 than the second proximal turns 64. The first proximal turns 54 of a serpentine band 20 are all circumferentially aligned with one another, and the second proximal turns 64 of a serpentine band 20 are all circumferentially aligned with one another.

Connector struts 16 may span from a first distal turn 56 to a first proximal turn 54.

The various struts 22 of a serpentine band 20 may have different longitudinal length components as measured in a direction parallel to the stent lengthwise axis 11 between the first end 21 and the second end 23 of the strut 22. Struts 22 that connect between a first proximal turn 54 and a first distal turn 56 may have a first longitudinal length component. Struts 22 that connect between a first proximal turn 54 and a second distal turn 66, and struts 22 that connect between a second proximal turn 64 and a first distal turn 64, may have a second longitudinal length component. The second longitudinal length component may be less than the first longitudinal length component. Struts 22 that connect between a second proximal turn 64 and a second distal turn 66 may have a third longitudinal length component. The third longitudinal length component may be less than the second longitudinal length component.

The serpentine bands 20 may alternatively be described as comprising alternating straight struts 30 and z-shaped struts 68, which may be connected to one another by alternating first proximal turns 54 and first distal turns 56. A z-shaped strut 68 may comprise a first portion 76, a second distal turn 66, a second portion 77, a second proximal turn 64 and a third portion 78. Each portion 76, 77, 78 may be straight along its length. The first portion 76 and the third portion 78 may be parallel or substantially parallel to one another, and may extend at an angle to the stent lengthwise axis 11. The second portion 77 may be oriented between the first portion 46 and the third portion 48, and may extend an angle to the stent lengthwise axis 11 different the first portion 46 or the third portion 48. In some embodiments, an angle between the stent lengthwise axis 11 and the first portion 46 may comprise a mirror image of an angle between the stent lengthwise axis 11 and the second portion 47, the mirror image taken across a line parallel to the stent lengthwise axis 11.

Figure 18:
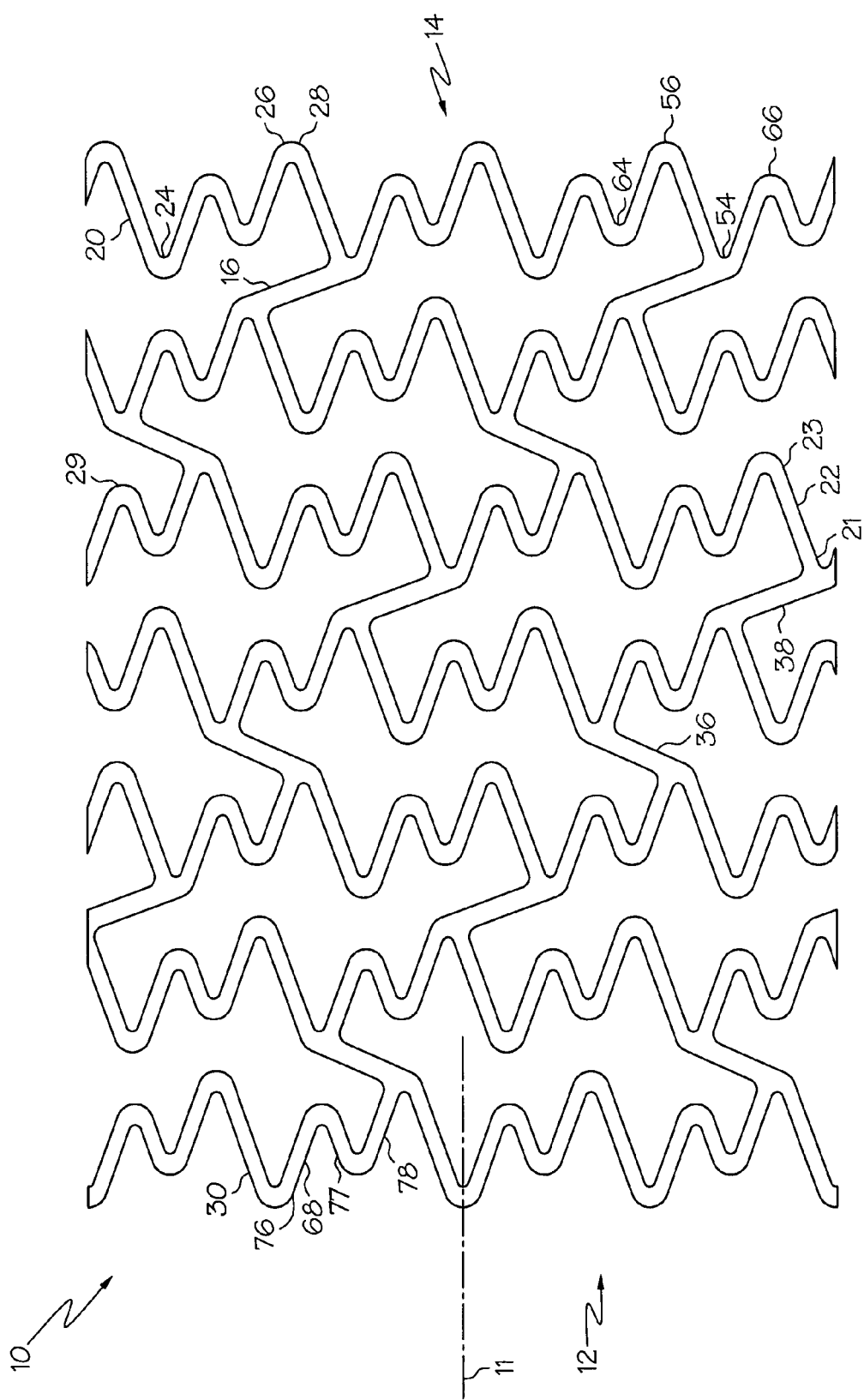

FIG. 18 shows an embodiment of a pattern for a stent 10 similar to the embodiment of FIG. 17, wherein the connector struts 16 further comprise a first type of connector strut 36 and a second type of connector strut 38. A first connector strut 36 extends in a first direction. A first connector strut 36 is oriented at a first angle to a stent lengthwise axis 11. A second connector strut 38 extends in a second direction that is different than or non-parallel to the first direction. Therefore, a second connector strut 38 is oriented at a second angle to a stent lengthwise axis 11, the second angle being different than the first angle. In some embodiments, the first angle and the second angle may have the same magnitude but different orientations. For example, a first connector strut 36 may form a 70° angle with a stent lengthwise axis 11, while a second connector strut 38 may form a negative 70° angle with the stent lengthwise axis 11. In some embodiments, a first angle may comprise a mirror image of a second angle across a line parallel to the stent lengthwise axis 11.

In some embodiments, all of the first connector struts 36 of the stent 10 may be parallel to one another. In some embodiments, a first connector strut 36 may extend between turns 28 which connect a straight strut 30 to a z-shaped strut 68. In some embodiments, each side of the first connector strut 36 may extend from a turn 28 in the direction of the side of the turn 28 which connects to a z-shaped strut 68.

In some embodiments, all of the second connector struts 38 of the stent 10 may be parallel to one another. In some embodiments, a second connector strut 38 may extend between turns 28 which connect a straight strut 30 to a z-shaped strut 68. In some embodiments, each side of the second connector strut 38 may extend from a turn 28 in the direction of the side of the turn 28 which connects to a straight strut 30.

Figure 19:
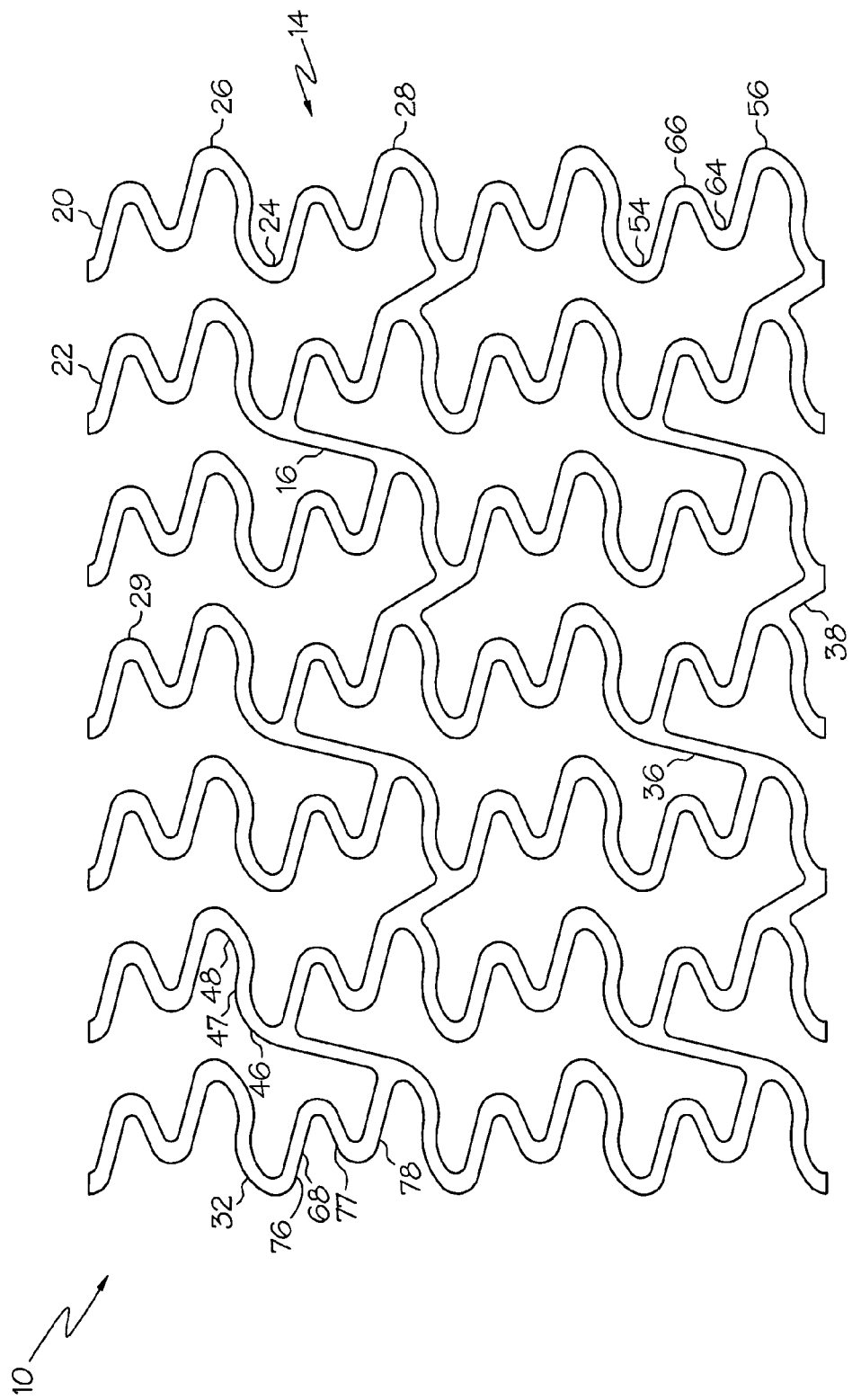
Figure 20:
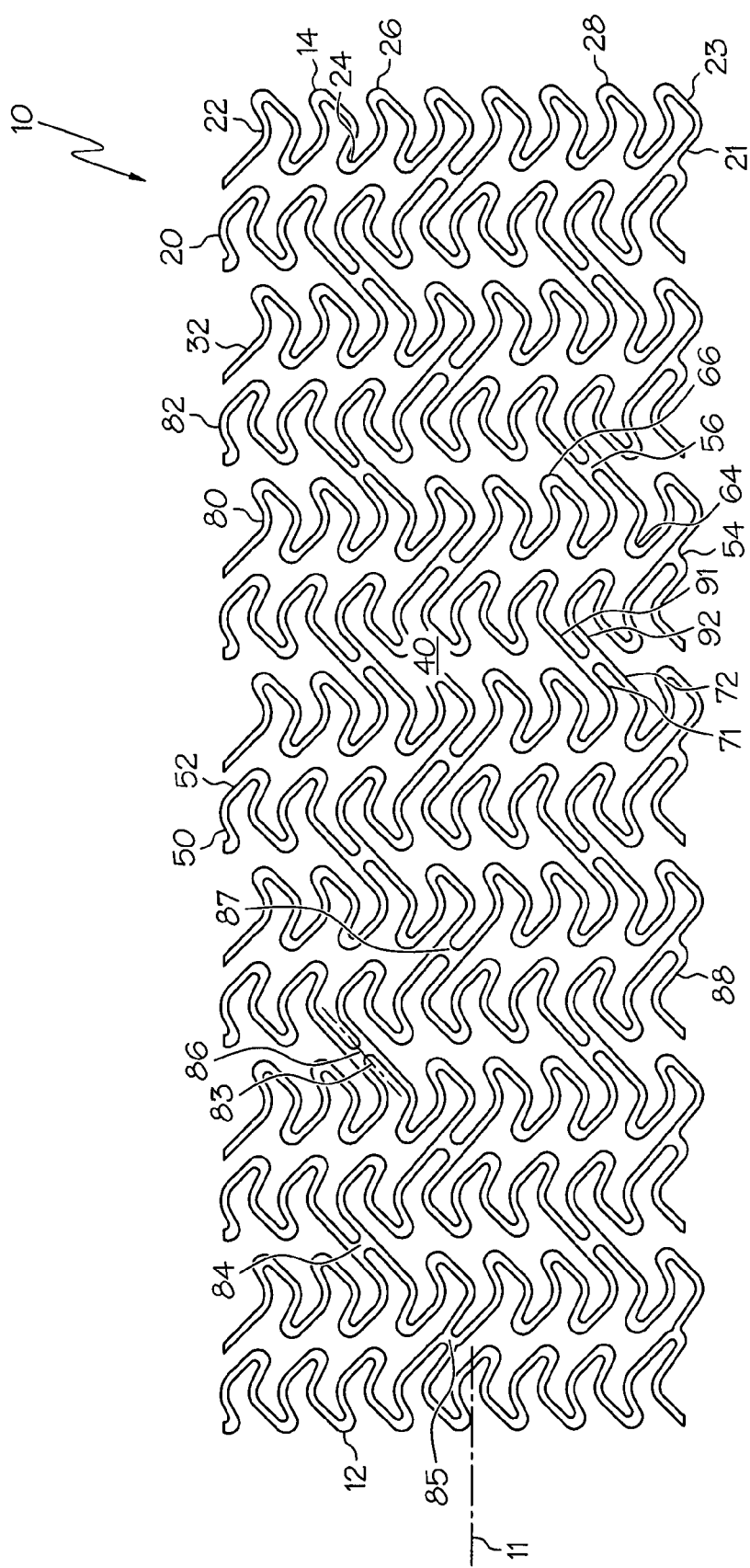
Figure 21:
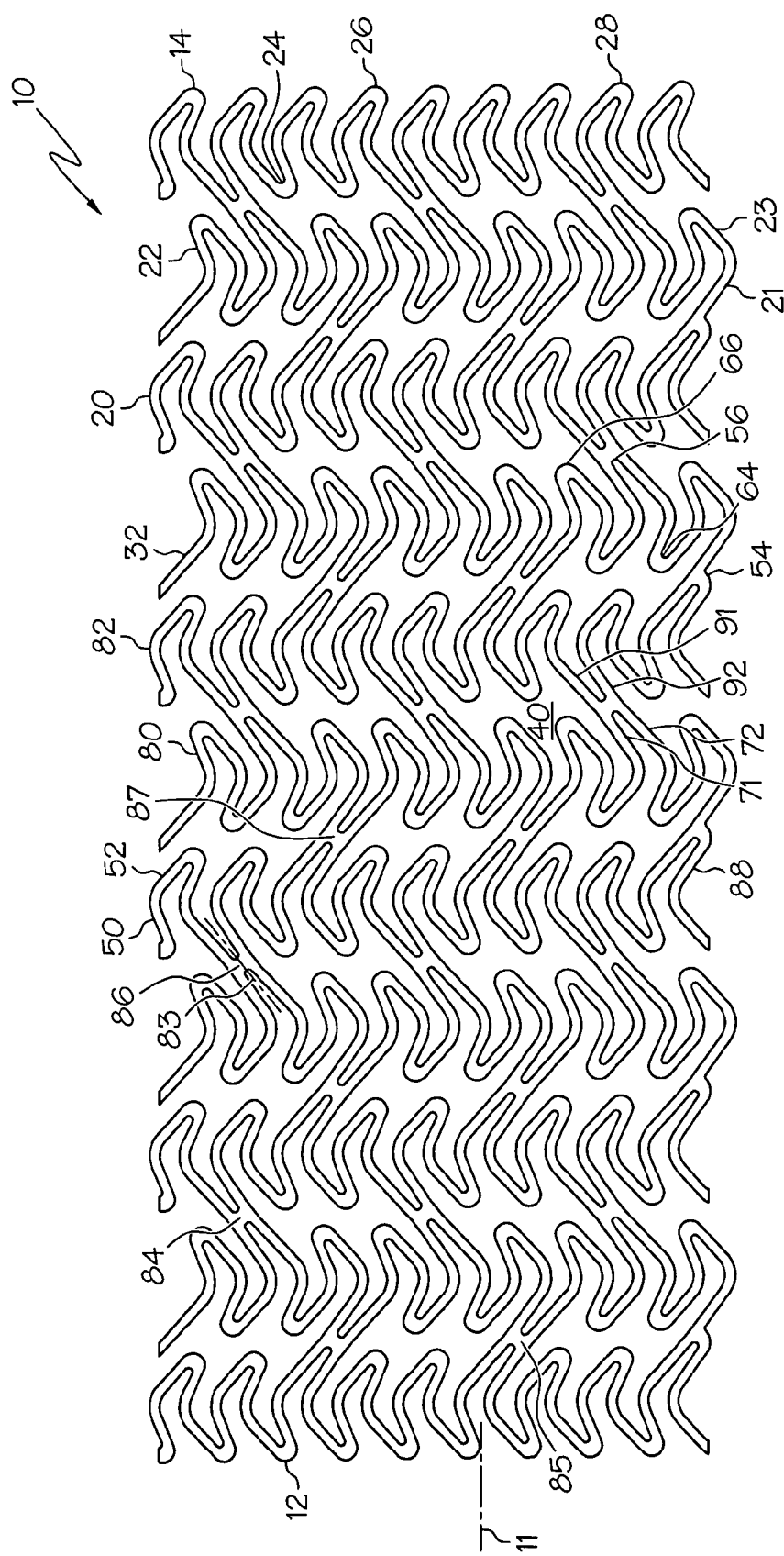
Figure 22:
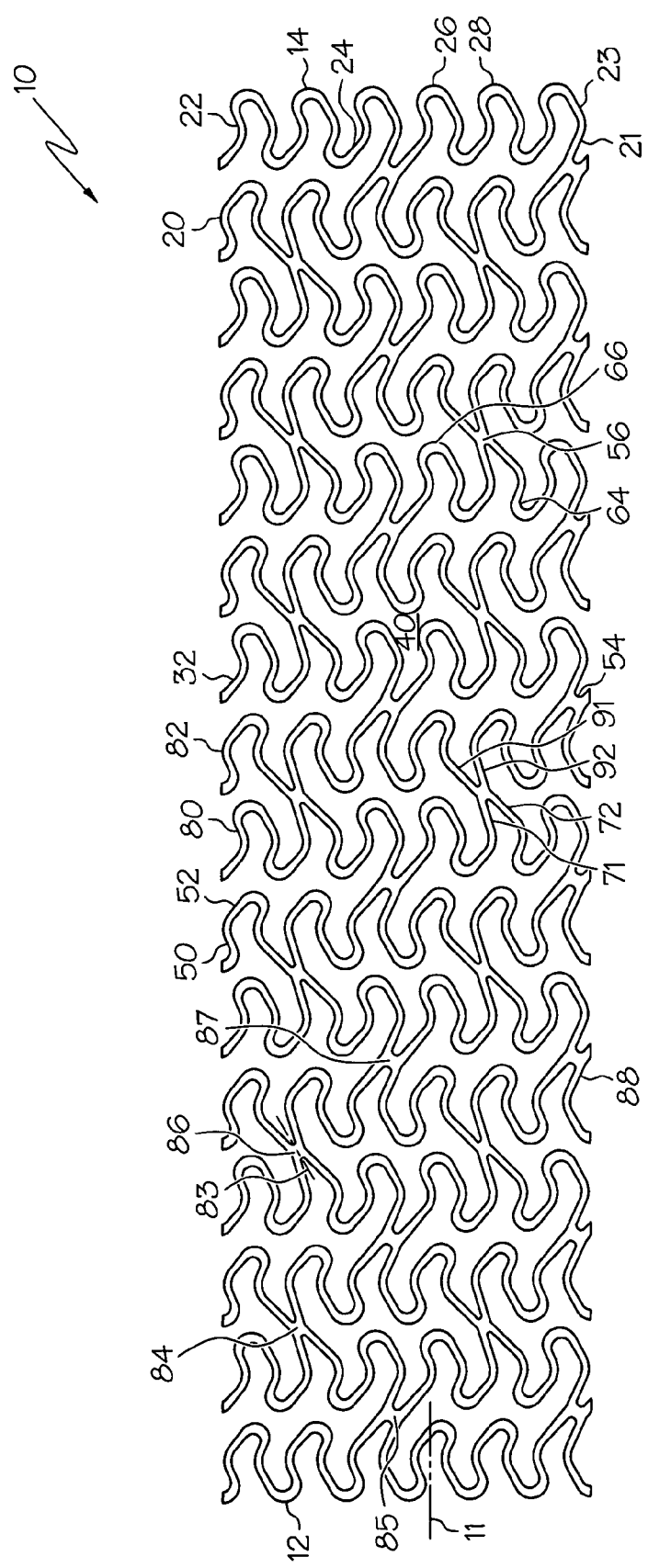
Figure 23:
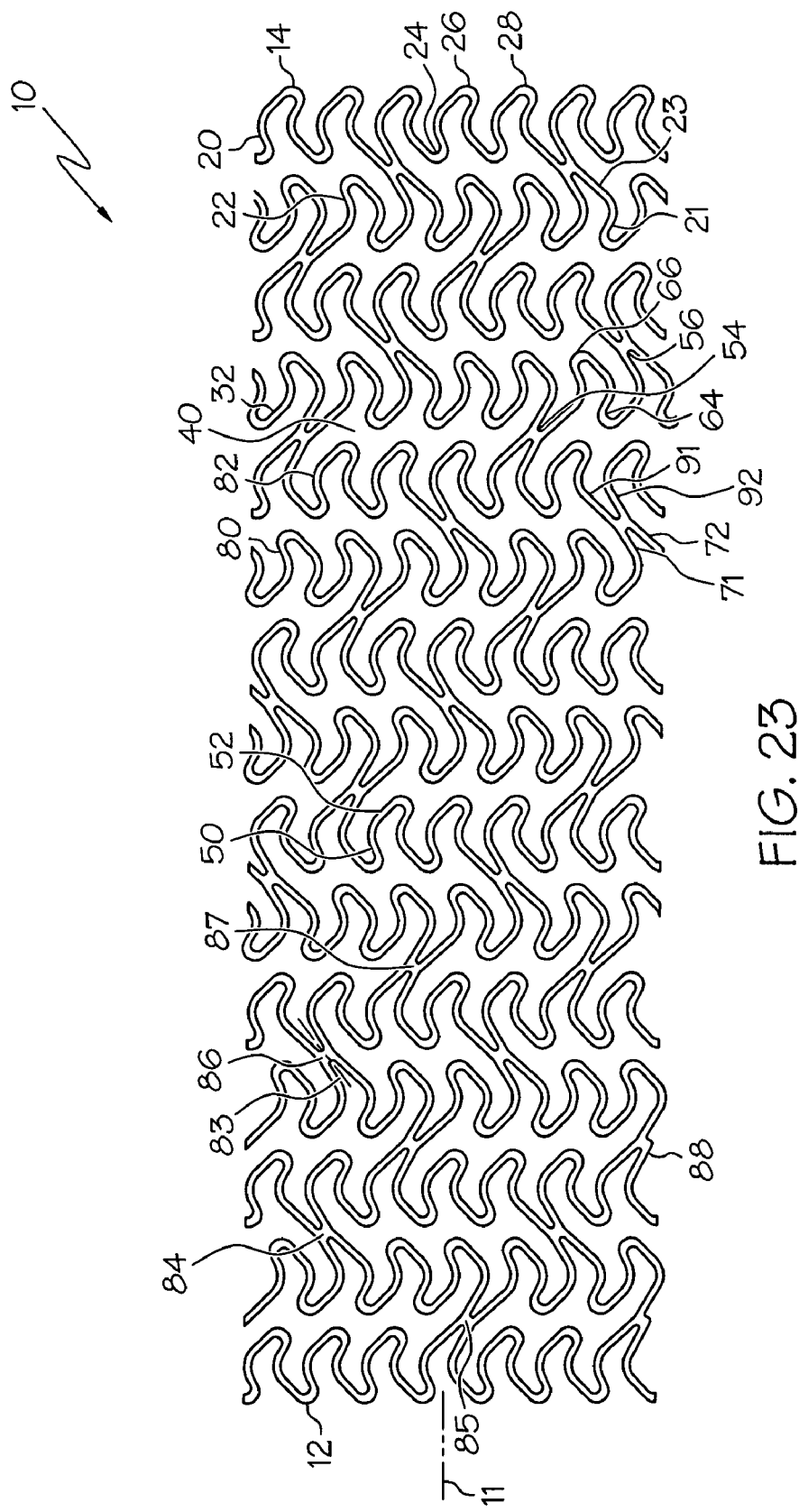
Figure 24:
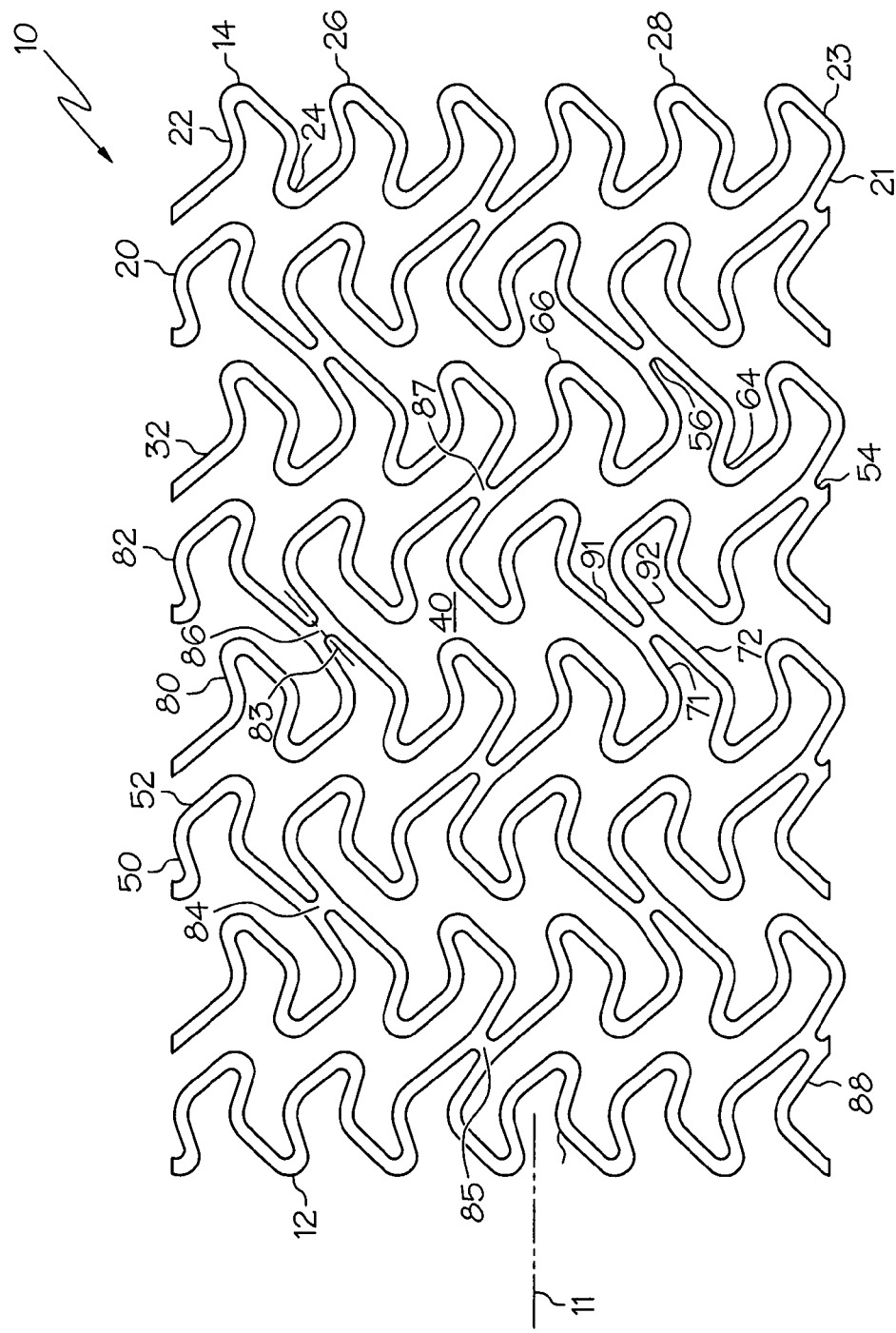
Figure 25:
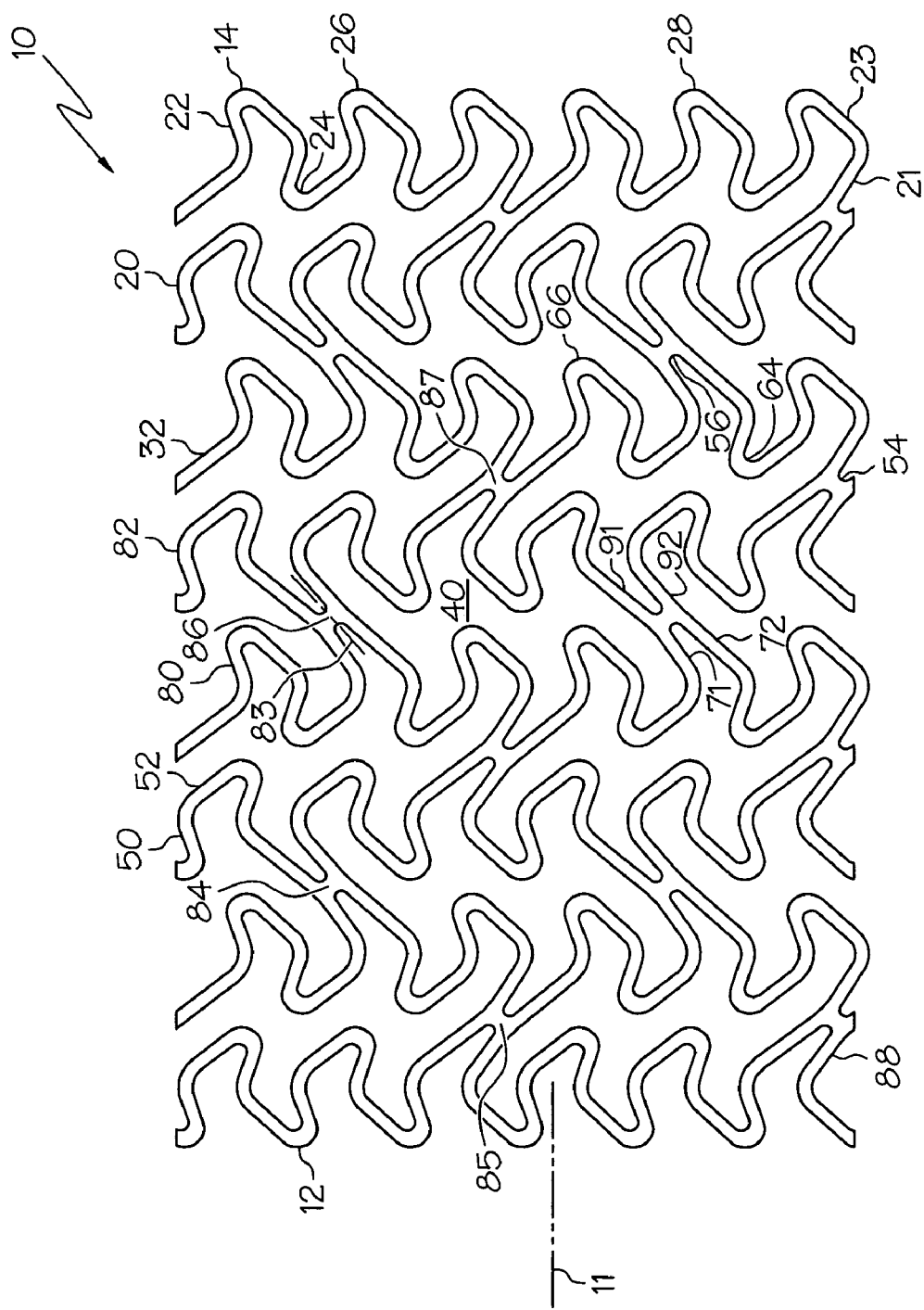
Figure 26:
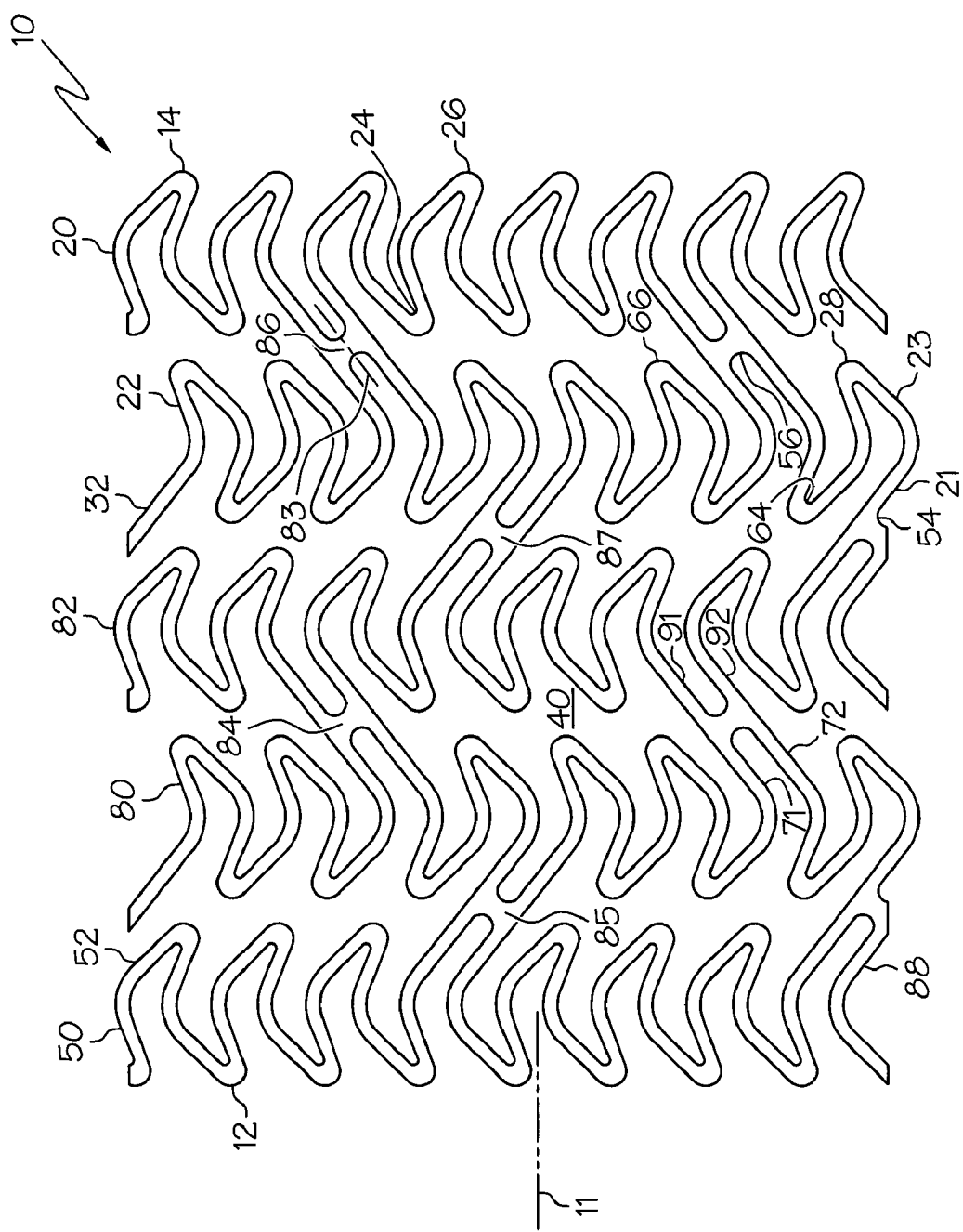
Figure 27:
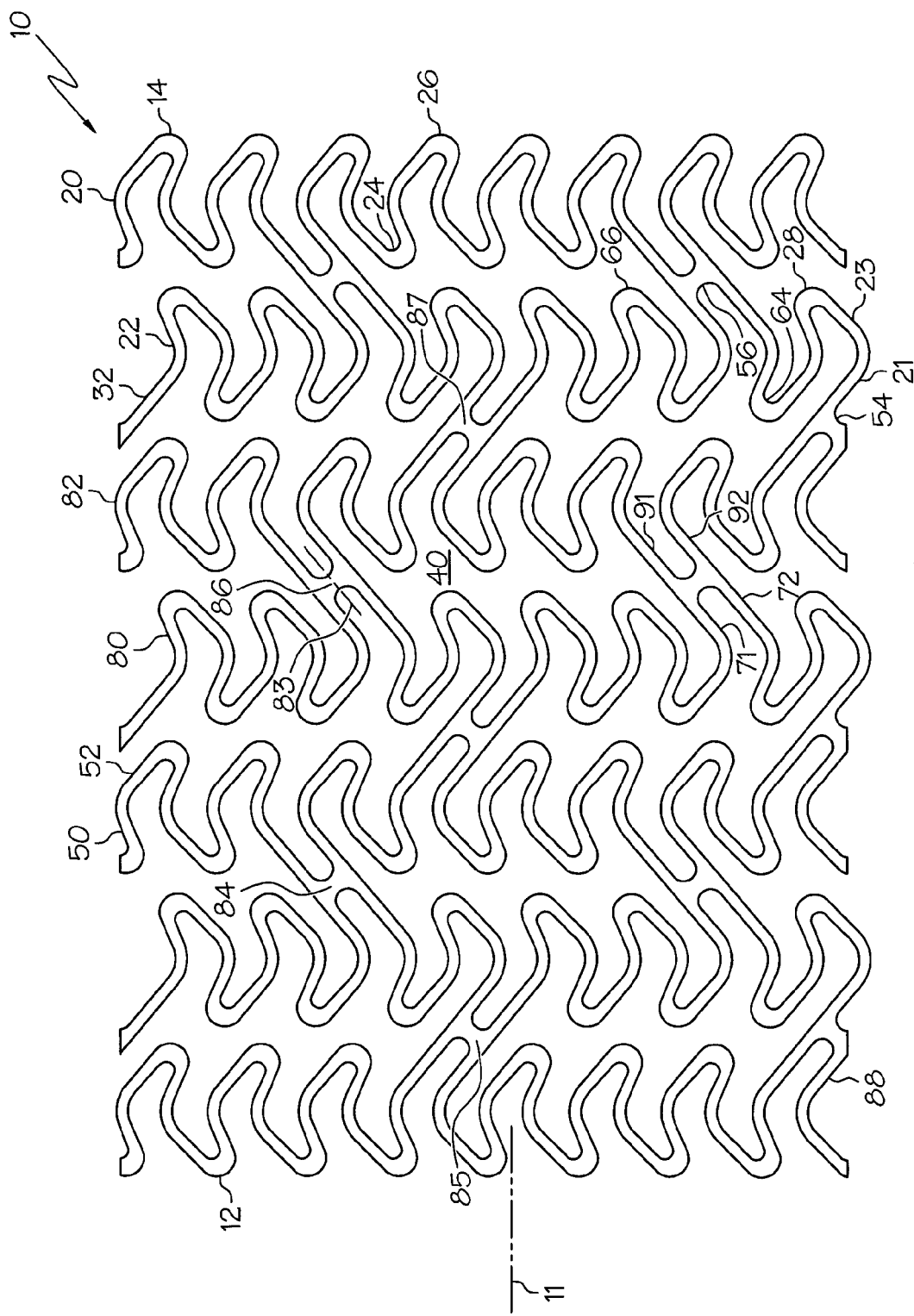

FIG. 19 shows an embodiment of a pattern for a stent 10 similar to the embodiment of FIG. 18, wherein the serpentine bands 20 comprise alternating s-shaped struts 32 and z-shaped struts 68 connected by alternating proximal peaks 24 and distal valleys 26.

Connector struts 16 span from a first distal turn 56 to a first proximal turn 54. The connector struts 16 further comprise a first type of connector strut 36 and a second type of connector strut 38. In some embodiments, a first connector strut 36 may extend between turns 28 which connect an s-shaped strut 32 to a z-shaped strut 68. In some embodiments, each side of the first connector strut 36 may extend from a turn 28 in the direction of the side of the turn 28 which connects to a z-shaped strut 68. In some embodiments, a second connector strut 38 may extend between turns 28 which connect a straight strut 30 to a z-shaped strut 68. In some embodiments, each side of the second connector strut 38 may extend from a turn 28 in the direction of the side of the turn 28 which connects to an s-shaped strut 32.

FIGS. 20-27 show various embodiments of flat patterns for a stent 10. As previously mentioned, like reference numerals in the Figures shall refer to like features as described herein. The various embodiments may comprise any suitable number of serpentine bands 20, any suitable number of struts 22 per serpentine band 20, any suitable number of turns 28 per serpentine band 20 and any suitable number of connections between adjacent serpentine bands 20. Struts 22 of a serpentine band 20 may have any suitable length, width and shape.

Referring to FIGS. 20-27, serpentine bands 20 comprise bent struts 32 connected by turns 28. Bent struts 32 comprise a first portion 50 and a second portion 52, wherein the first portion 50 is oriented at an angle to the second portion 52.

Serpentine bands 20 further comprise first serpentine bands 80 and second serpentine bands 82. Bent struts 32 included in a first serpentine band 80 have curvature of a first general orientation. Bent struts 32 included in a second serpentine band 82 have curvature of a second general orientation that is different than first general orientation, and may be substantially opposite to the first general orientation. For example, from a given reference point, if the bent struts 32 included in a first serpentine band 80 may be considered convex, the bent struts 32 included in a second serpentine band 82 may be considered concave. Within the first general orientation, adjacent bent struts 32 of a first serpentine band 80 may have a slightly different orientation, for example being rotated with respect to one another. Within the second general orientation, adjacent bent struts 32 of a second serpentine band 82 may have a slightly different orientation, for example being slightly rotated with respect to one another.

Each turn 28 has a width, and the width of a turn 28 may be greater than the width of one or more struts 22 of the stent 10. The width of a turn 28 may increase from a strut 22 width at its ends and reach a maximum at a midpoint of the turn 28. In some embodiments, the width of a turn 28 may be less than the width of one or more struts 22 of the stent 10, and the width of a turn 28 may decrease from a strut 22 width at its ends and reach a minimum at a midpoint of the turn 28.

The proximal turns 24 of a serpentine band 20 may comprise first proximal turns 54 and second proximal turns 64. The distal turns 26 of a serpentine band 20 may comprise first distal turns 56 and second distal turns 66. The first distal turns 56 of a serpentine band 20 may extend farther toward the distal end 14 of the stent 10 than the second distal turns 66. The second distal turns 66 of a serpentine band 20 may all be circumferentially aligned with one another. Similarly, the first proximal turns 54 of a serpentine band 20 may extend farther toward the proximal end 12 of the stent 10 than the second proximal turns 64. The second proximal turns 64 of a serpentine band 20 may all be circumferentially aligned with one another.

Various struts 22 of a serpentine band 20 may have different longitudinal length components as measured in a direction parallel to the stent lengthwise axis 11 between the first end 21 and the second end 23 of the strut 22. Struts 22 that connect to a first proximal turn 54 or to a first distal turn 56 may have a first longitudinal length component. Struts 22 that connect between a second proximal turn 64 and a second distal turn 66 may have a second longitudinal length component. The second longitudinal length component may be less than the first longitudinal length component.

Adjacent serpentine bands 20 are connected by at least one connection 84. Connections 84 may comprise a first distal turn 56 that is attached to a first proximal turn 54.

Struts 22 that connect to a connection 84, or to a first proximal turn 54 or a first distal turn 56, are longer than other struts 22 of a serpentine band 20 and may comprise an extended strut 88. Extended struts 88 have a longer longitudinal length component than other struts 22 of a serpentine band. Multiple extended struts 88 meet at a connection 84, and along with a linking member 85 may generally form an H-shape.

The extended struts 88 of an H-shaped connection 84 comprise a first proximal portion 71, a second proximal portion 72, a first distal portion 91 and a second distal portion 92. In some embodiments, the first proximal portion 71 may be parallel to the second distal portion 92, and the second proximal portion 72 may be parallel to the first distal portion 91. In some embodiments, the first proximal portion 71 may be nonparallel to the second proximal portion 72, and the first distal portion 91 may be nonparallel to the second distal portion 92.

In some embodiments, the H-shaped connections 84 may comprise first connections 86 and second connections 87. A first connection 86 may have a first orientation and a second connection may have a second orientation that is different from the first orientation. For example, a first connection 86 may have an axis 83 that may comprise a "vertical" axis of the H-shape. The axis 83 may be oriented at a first angle to a stent lengthwise axis 11. An axis 83 of a second connection 87 may be oriented at a second angle to a stent lengthwise axis 11, the second angle being different than the first angle. In some embodiments, the first angle and the second angle may have the same magnitude but different orientations. For example, an axis 83 of a first connection 86 may form a 40° angle with a stent lengthwise axis 11, while an axis 83 of a second connection 87 may form a negative 40° angle with the stent lengthwise axis 11. In some embodiments, a first angle may comprise a mirror image of a second angle across a line parallel to the stent lengthwise axis 11.

In some embodiments, a first connection 86 may comprise a first distal turn 56 of a first serpentine band 80 that is connected to a first proximal turn 54 of a second serpentine band 82. In some embodiments, a second connection 87 may comprise a first distal turn 56 of a second serpentine band 82 that is connected to a first proximal turn 54 of a first serpentine band 80.

Further, a first proximal portion 71 may comprise a substantial mirror image of a second proximal portion 72 taken across an axis 83 of the connection 84. A first distal portion 91 may comprise a substantial mirror image of a second proximal portion 72 taken across an axis 83 of the connection 84.

Figure 28:
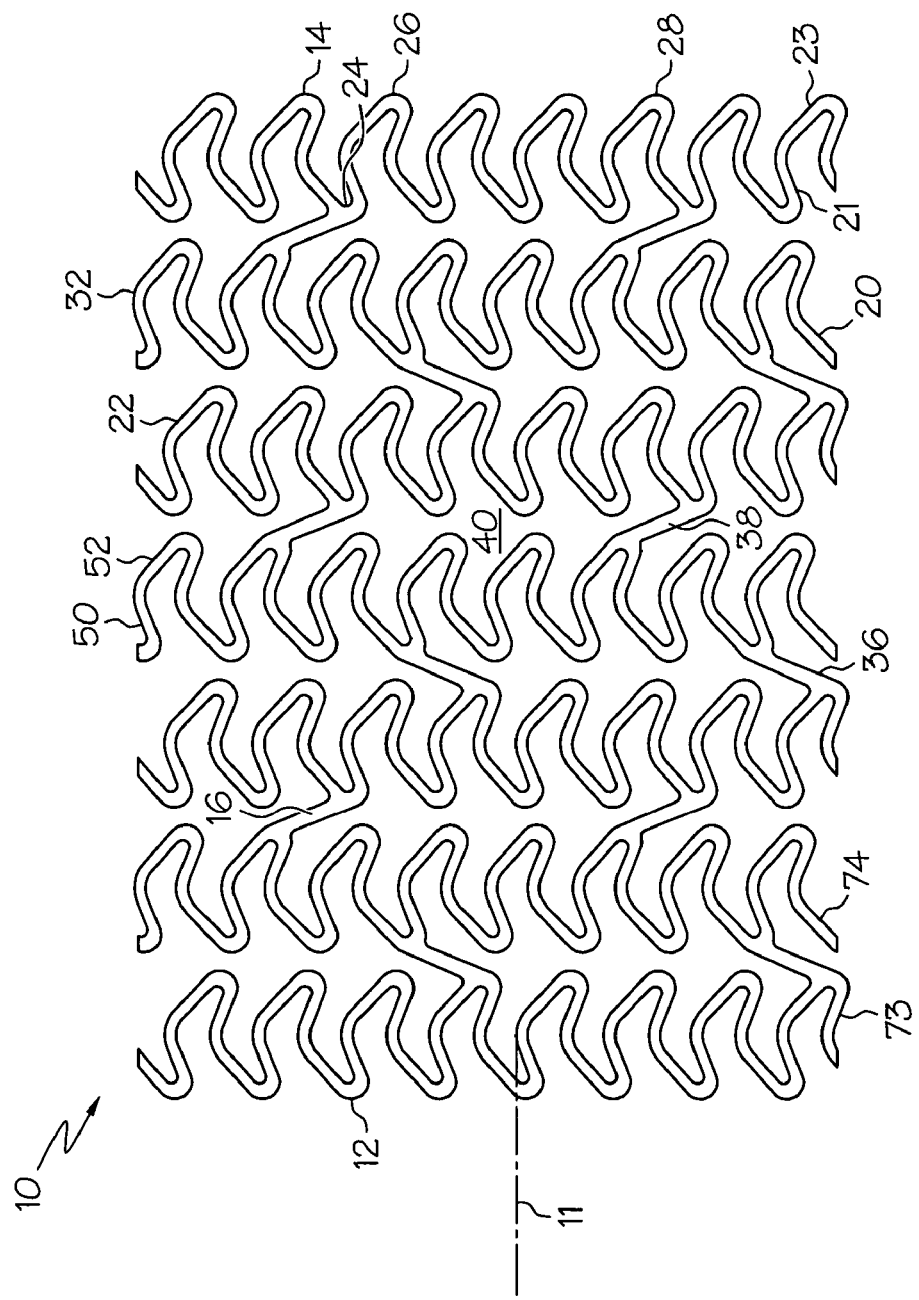

FIG. 28 shows another embodiment of a flat pattern for a stent 10 comprising a plurality of serpentine bands 20. Each serpentine band 20 includes a plurality of bent struts 32. Each bent strut 32 comprises a first portion 50 and a second portion 52. The first portion 50 extends at an angle to the stent lengthwise axis 11, and the second portion 52 extends at another angle to the stent lengthwise axis 11.

Each turn 28 may have a width, and the width of a turn 28 may be greater than the width of one or more struts 22 of the stent 10. The width of a turn 28 may increase from a strut 22 width at its ends and reach a maximum at a midpoint of the turn 28. In some embodiments, the width of a turn 28 may be less than the width of one or more struts 22 of the stent 10, and the width of a turn 28 may decrease from a strut 22 width at its ends and reach a minimum at a midpoint of the turn 28.

Serpentine bands 20 comprise first serpentine bands 73 and second serpentine bands 74. First serpentine bands 73 and second serpentine bands 74 alternate along the length of the stent 10.

Connector struts 16 comprise first connector struts 36 and second connector struts 38. First connector struts 36 connect between a distal valley 26 of a first serpentine band 73 and a proximal peak 24 of a second serpentine band 74. Second connector struts 38 connect between a distal valley 26 of a second serpentine band 74 and a proximal peak 24 of a first serpentine band 73.

Figure 29:
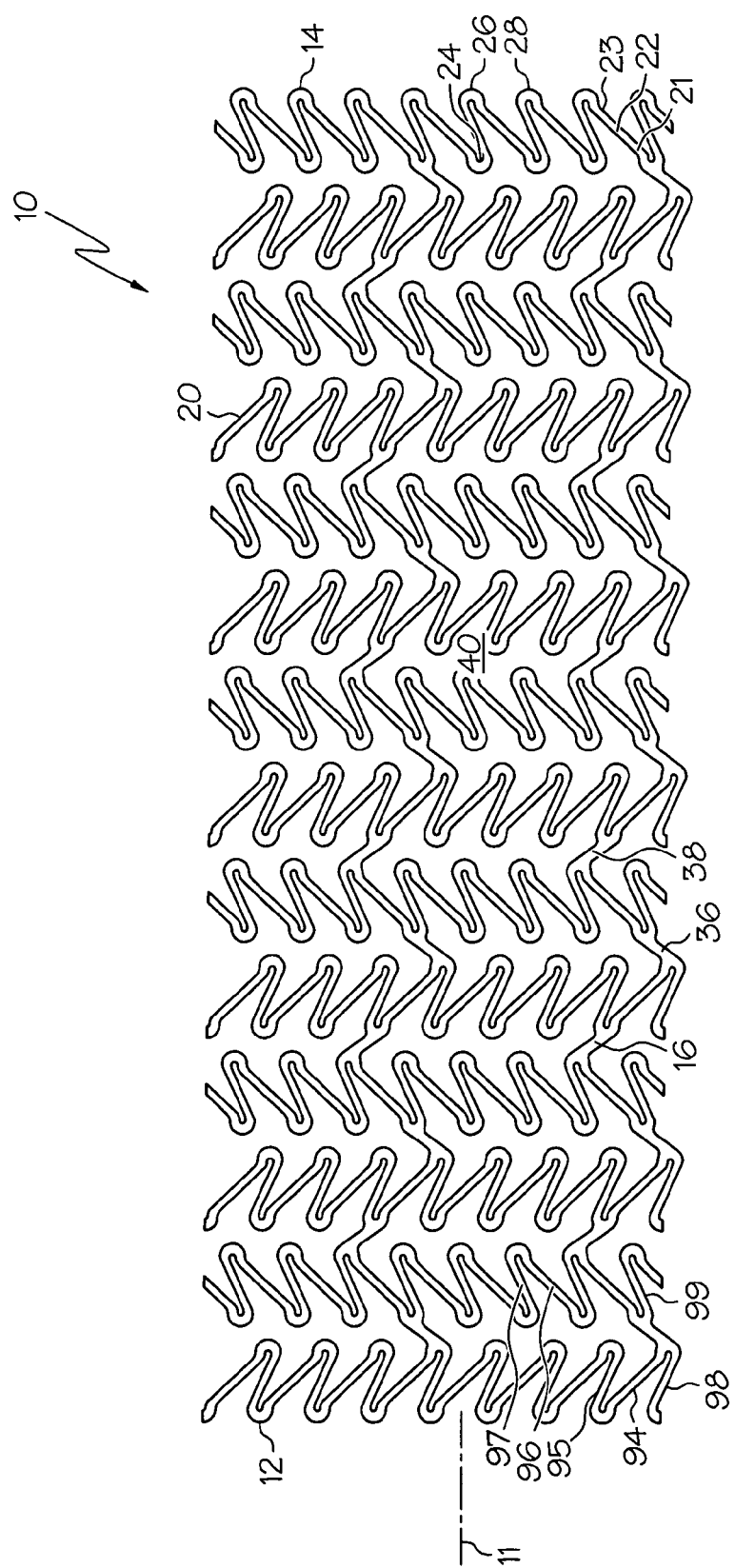

FIG. 29 shows another embodiment of a flat pattern for a stent 10 comprising serpentine bands 20 connected by connector struts 16. Serpentine bands 20 comprise first serpentine bands 98 and second serpentine bands 99. First serpentine bands 98 and second serpentine bands 99 alternate along the length of the stent 10.

First serpentine bands 98 comprise alternating first struts 94 and second struts 95 connected by turns 28. The first struts 94 are oriented at an angle to the second struts 95. Second serpentine bands 99 comprise alternating third struts 96 and fourth struts 97 connected by turns 28. The third struts 96 are oriented at an angle to the fourth struts 97. An angle between a first strut 94 and a line parallel to the stent lengthwise axis 11 may comprise a mirror image of an angle between a third strut 96 and a line parallel to the stent lengthwise axis 11 taken across a circumferential line. An angle between a second strut 95 and a line parallel to the stent lengthwise axis 11 may comprise a mirror image of an angle between a fourth strut 97 and a line parallel to the stent lengthwise axis 11 taken across a circumferential line.

Each turn 28 may have a width, and the width of a turn 28 may be greater than the width of one or more struts 22 of the stent 10. The width of a turn 28 may increase from a strut 22 width at its ends and reach a maximum at a midpoint of the turn 28. In some embodiments, the width of a turn 28 may be less than the width of one or more struts 22 of the stent 10, and the width of a turn 28 may decrease from a strut 22 width at its ends and reach a minimum at a midpoint of the turn 28.

Connector struts 16 comprise first connector struts 36 and second connector struts 38. First connector struts 36 connect between a distal valley 26 of a first serpentine band 98 and a proximal peak 24 of a second serpentine band 99. Second connector struts 38 connect between a distal valley 26 of a second serpentine band 99 and a proximal peak 24 of a first serpentine band 98.

Figure 30:
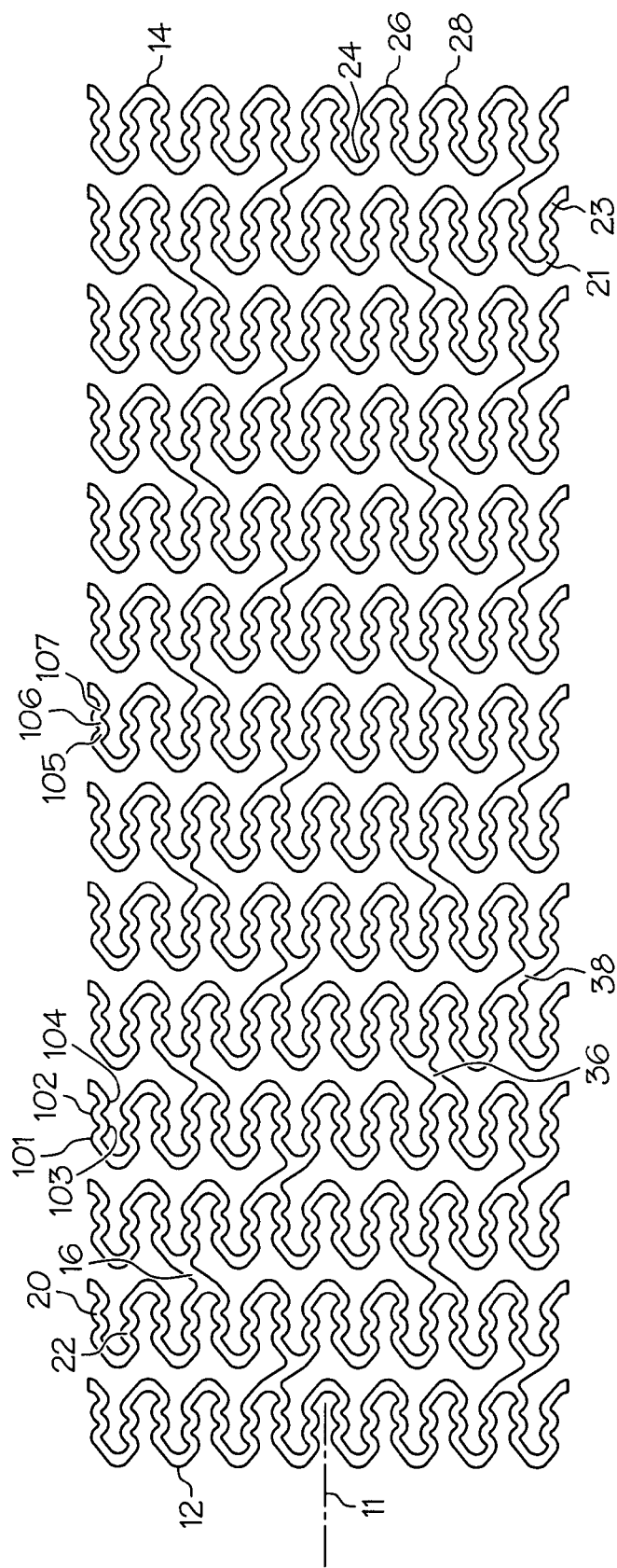

FIG. 30 shows another embodiment of a flat pattern for a stent 10 comprising a plurality of serpentine bands 20 connected by connector struts 16. Connector struts 16 comprise first connector struts 36 and second connector struts 38.

A strut 22 includes a wavelike shape, and may include a plurality of portions of alternating concavity. A strut 22 comprises a first maximum 101, a second maximum 102, a first minimum 103 and a second minimum 104. A strut 22 further comprise a first inflection point 105, a second inflection point 106 and a third inflection point 107. Each inflection point 105, 106, 107 may comprise a change in concavity of the strut 22.

Each turn 28 may have a width, and the width of a turn 28 may be greater than the width of one or more struts 22 of the stent 10. The width of a turn 28 may increase from a strut 22 width at its ends and reach a maximum at a midpoint of the turn 28. In some embodiments, the width of a turn 28 may be less than the width of one or more struts 22 of the stent 10, and the width of a turn 28 may decrease from a strut 22 width at its ends and reach a minimum at a midpoint of the turn 28.

Figure 31:
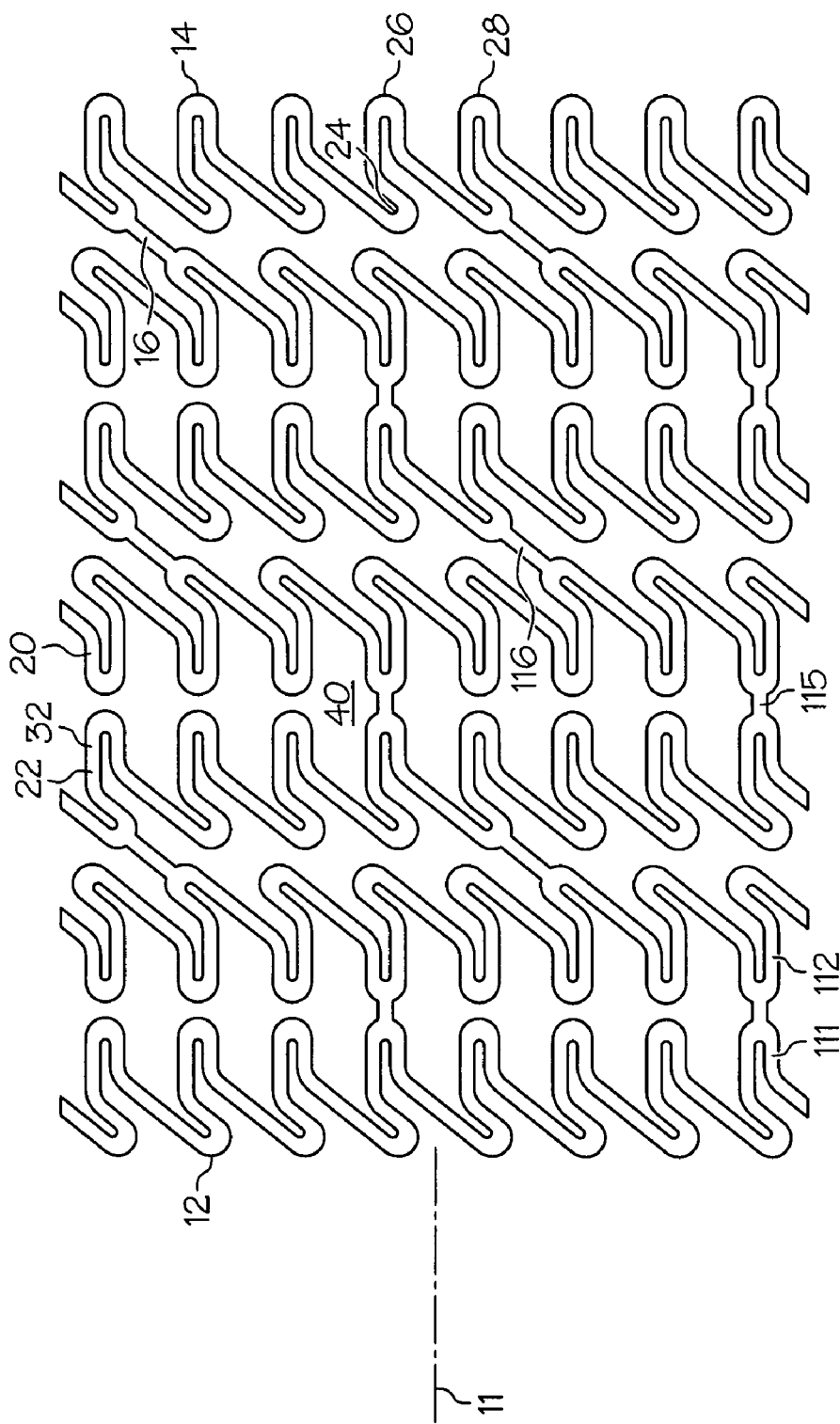

FIG. 31 shows another embodiment of a flat pattern for a stent 10 comprising a plurality of serpentine bands 20 connected by connector struts 16. Struts 22 of a serpentine band 20 comprise bent struts 32.

Serpentine bands 20 comprise first serpentine bands 111 and second serpentine bands 112 having a different orientation than the first serpentine bands 111. First serpentine bands 111 and second serpentine bands 112 alternate along the length of the stent 10.

Connector struts 16 comprise first connector struts 115 and second connector struts 116. First connector struts 115 are parallel to the stent lengthwise axis 11, while second connector struts 116 are oriented at an angle to the stent lengthwise axis 11.

A first connector strut 115 connects between a distal valley 26 of a first serpentine band 111 and a proximal peak 24 of a second serpentine band 112. A second connector strut 116 connects between a distal valley 26 of a second serpentine band 112 and a proximal peak 24 of a first serpentine band 111.

A cell 40 that is partially bounded by a first connector strut 115 may comprise a different shape than a cell 40 that is partially bounded by a second connector strut 116.

In some embodiments, for example as may be shown in FIGS. 1-11, a stent 10 may be described by the following numbered paragraphs:

1. A stent comprising a plurality of interconnected serpentine bands, each serpentine band having alternating straight struts and s-shaped struts forming peaks and valleys, each straight strut connected at one end to one s-shaped strut and at a second end to a second s-shaped strut, each s-shaped strut connected at one end to one straight strut and at a second end to a second straight strut, one end of the s-shaped struts connected to one end of the straight struts at a peak and another end of the s-shaped struts connected to one end of the straight strut at a valley, adjacent serpentine bands connected by a plurality of linear connectors, the linear connectors extending from peaks of one serpentine band to valleys of a serpentine band adjacent thereto.

2. The stent of paragraph 1, further comprising first serpentine bands having a first orientation and second serpentine bands having a second orientation that is different from the first orientation.

3. The stent of paragraph 2, wherein first serpentine bands and second serpentine bands alternate along the length of the stent.

4. The stent of paragraph 3, further comprising first linear connectors and second linear connectors, the second linear connectors being nonparallel to the first linear connectors.

5. The stent of paragraph 4, wherein all of the first linear connectors are parallel to one another.
6. The stent of paragraph 5, wherein all of the second linear connectors are parallel to one another.
7. The stent of paragraph 4, wherein a first angle between a first linear connector and a stent lengthwise axis comprises a substantial mirror image of a second angle between a second linear connector and a stent lengthwise axis, the substantial mirror image taken across a stent circumferential line.
8. The stent of paragraph 4, wherein the first linear connectors extend from a valley of a first serpentine band to a peak of a second serpentine band.
9. The stent of paragraph 8, wherein the first linear connectors extend from the valley in a direction of a side of the valley comprising the s-shaped strut.
10. The stent of paragraph 8, wherein the second linear connectors extend from a valley of a second serpentine band to a peak of a first serpentine band.
11. The stent of paragraph 10, wherein the second linear connectors extend from the valley in a direction of a side of the valley comprising the straight strut.
12. The stent of paragraph 1, wherein a straight strut comprises a width, and a valley connected to the straight strut comprises a width that is greater than the width of the straight strut.
13. The stent of paragraph 1, wherein each valley of a serpentine band is aligned about a circumference of the stent.
14. The stent of paragraph 1, wherein a serpentine band comprises first peaks and second peaks, the first peaks being aligned about a first circumference of the stent, the second peaks being aligned about a second circumference of the stent that is offset from the first circumference.
15. The stent of paragraph 14, wherein the serpentine band having first peaks and second peaks further comprises first valleys and second valleys, the first valleys being aligned about a third circumference of the stent, the second valleys being aligned about a fourth circumference of the stent that is offset from the third circumference.

In some embodiments, for example as may be shown in FIGS. 1-11, a stent 10 may be described by the following numbered paragraphs:

1. A stent comprising a plurality of interconnected serpentine bands,
   each serpentine band having alternating straight struts and s-shaped struts forming peaks and valleys, each straight strut connected at one end to one s-shaped strut and at a second end to a second s-shaped strut, each s-shaped strut connected at one end to one straight strut and at a second end to a second straight strut, one end of the s-shaped struts connected to one end of the straight struts at a peak and another end of the s-shaped struts connected to one end of the straight strut at a valley,
   adjacent serpentine bands connected by a plurality of linear connectors, the connectors extending from peaks of one band to valleys of a band adjacent thereto,
   the serpentine bands and connectors defining a plurality of cells, each cell including a plurality of unconnected peaks and valleys, the unconnected peaks disposed on one serpentine band, the unconnected valleys disposed on the adjacent serpentine band.
2. The stent of paragraph 1, further comprising first serpentine bands having a first orientation and second serpentine bands having a second orientation that is different from the first orientation.
3. The stent of paragraph 2, wherein first serpentine bands and second serpentine bands alternate along the length of the stent.
4. The stent of paragraph 3, further comprising first linear connectors and second linear connectors, the second linear connectors being nonparallel to the first linear connectors.
5. The stent of paragraph 4, wherein all of the first linear connectors are parallel to one another.
6. The stent of paragraph 5, wherein all of the second linear connectors are parallel to one another.
7. The stent of paragraph 4, wherein a first angle between a first linear connector and a stent lengthwise axis comprises a substantial mirror image of a second angle between a second linear connector and a stent lengthwise axis, the substantial mirror image taken across a stent circumferential line.
8. The stent of paragraph 4, wherein the first linear connectors extend from a valley of a first serpentine band to a peak of a second serpentine band.
9. The stent of paragraph 8, wherein the first linear connectors extend from the valley in a direction of a side of the valley comprising the s-shaped strut.
10. The stent of paragraph 8, wherein the second linear connectors extend from a valley of a second serpentine band to a peak of a first serpentine band.
11. The stent of paragraph 10, wherein the second linear connectors extend from the valley in a direction of a side of the valley comprising the straight strut.
12. The stent of paragraph 1, wherein a straight strut comprises a width, and a valley connected to the straight strut comprises a width that is greater than the width of the straight strut.
13. The stent of paragraph 1, wherein each valley of a serpentine band is aligned about a circumference of the stent.
14. The stent of paragraph 1, wherein a serpentine band comprises first peaks and second peaks, the first peaks being aligned about a first circumference of the stent, the second peaks being aligned about a second circumference of the stent that is offset from the first circumference.
15. The stent of paragraph 14, wherein the serpentine band having first peaks and second peaks further comprises first valleys and second valleys, the first valleys being aligned about a third circumference of the stent, the second valleys being aligned about a fourth circumference of the stent that is offset from the third circumference.

In some embodiments, for example as may be shown in FIGS. 1-11, a stent 10 may be described by the following numbered paragraphs:

1. A stent comprising a plurality of interconnected serpentine bands,
   each serpentine band having alternating straight struts and s-shaped struts forming peaks and valleys, each straight strut connected at one end to one s-shaped strut and at a second end to a second s-shaped strut, each s-shaped strut connected at one end to one straight strut and at a second end to a second straight strut, one end of the s-shaped struts connected to one end of the straight struts at a peak and another end of the s-shaped struts connected to one end of the straight strut at a valley,
   adjacent serpentine bands connected by a plurality of connectors, the connectors extending from peaks of one serpentine band to valleys of a serpentine band adjacent thereto,
   the connectors including a first connector extending in a first direction and a second connector extending in a second direction which is non-parallel to the first direction.

2. The stent of paragraph 1, further comprising first serpentine bands having a first orientation and second serpentine bands having a second orientation that is different from the first orientation.
3. The stent of paragraph 2, wherein first serpentine bands and second serpentine bands alternate along the length of the stent.
4. The stent of paragraph 3, further comprising first linear connectors and second linear connectors, the second linear connectors being nonparallel to the first linear connectors.
5. The stent of paragraph 4, wherein all of the first linear connectors are parallel to one another.
6. The stent of paragraph 5, wherein all of the second linear connectors are parallel to one another.
7. The stent of paragraph 4, wherein a first angle between a first linear connector and a stent lengthwise axis comprises a substantial mirror image of a second angle between a second linear connector and a stent lengthwise axis, the substantial mirror image taken across a stent circumferential line.
8. The stent of paragraph 4, wherein the first linear connectors extend from a valley of a first serpentine band to a peak of a second serpentine band.
9. The stent of paragraph 8, wherein the first linear connectors extend from the valley in a direction of a side of the valley comprising the s-shaped strut.
10. The stent of paragraph 8, wherein the second linear connectors extend from a valley of a second serpentine band to a peak of a first serpentine band.
11. The stent of paragraph 10, wherein the second linear connectors extend from the valley in a direction of a side of the valley comprising the straight strut.
12. The stent of paragraph 1, wherein a straight strut comprises a width, and a valley connected to the straight strut comprises a width that is greater than the width of the straight strut.
13. The stent of paragraph 1, wherein each valley of a serpentine band is aligned about a circumference of the stent.
14. The stent of paragraph 1, wherein a serpentine band comprises first peaks and second peaks, the first peaks being aligned about a first circumference of the stent, the second peaks being aligned about a second circumference of the stent that is offset from the first circumference.
15. The stent of paragraph 14, wherein the serpentine band having first peaks and second peaks further comprises first valleys and second valleys, the first valleys being aligned about a third circumference of the stent, the second valleys being aligned about a fourth circumference of the stent that is offset from the third circumference.

In some embodiments, for example as may be shown in FIGS. 5, 6, 8 and 11, a stent 10 may be described by the following numbered paragraphs:

1. A stent comprising a plurality of interconnected serpentine bands,
    each serpentine band having alternating straight struts and s-shaped struts forming peaks and valleys, each straight strut connected at one end to one s-shaped strut and at a second end to a second s-shaped strut, each s-shaped strut connected at one end to one straight strut and at a second end to a second straight strut, one end of the s-shaped struts connected to one end of the straight struts at a peak and another end of the s-shaped struts connected to one end of the straight strut at a valley,
    adjacent serpentine bands connected by a plurality of connectors, to form cells, cells which are circumferentially adjacent one another being of different sizes.

2. The stent of paragraph 1, further comprising first serpentine bands having a first orientation and second serpentine bands having a second orientation that is different from the first orientation.
3. The stent of paragraph 2, wherein first serpentine bands and second serpentine bands alternate along the length of the stent.
4. The stent of paragraph 3, further comprising first linear connectors and second linear connectors, the second linear connectors being nonparallel to the first linear connectors.
5. The stent of paragraph 4, wherein all of the first linear connectors are parallel to one another.
6. The stent of paragraph 5, wherein all of the second linear connectors are parallel to one another.
7. The stent of paragraph 4, wherein a first angle between a first linear connector and a stent lengthwise axis comprises a substantial mirror image of a second angle between a second linear connector and a stent lengthwise axis, the substantial mirror image taken across a stent circumferential line.
8. The stent of paragraph 4, wherein the first linear connectors extend from a valley of a first serpentine band to a peak of a second serpentine band.
9. The stent of paragraph 8, wherein the first linear connectors extend from the valley in a direction of a side of the valley comprising the s-shaped strut.
10. The stent of paragraph 8, wherein the second linear connectors extend from a valley of a second serpentine band to a peak of a first serpentine band.
11. The stent of paragraph 10, wherein the second linear connectors extend from the valley in a direction of a side of the valley comprising the straight strut.
12. The stent of paragraph 1, wherein a straight strut comprises a width, and a valley connected to the straight strut comprises a width that is greater than the width of the straight strut.
13. The stent of paragraph 1, wherein each valley of a serpentine band is aligned about a circumference of the stent.
14. The stent of paragraph 1, wherein a serpentine band comprises first peaks and second peaks, the first peaks being aligned about a first circumference of the stent, the second peaks being aligned about a second circumference of the stent that is offset from the first circumference.
15. The stent of paragraph 14, wherein the serpentine band having first peaks and second peaks further comprises first valleys and second valleys, the first valleys being aligned about a third circumference of the stent, the second valleys being aligned about a fourth circumference of the stent that is offset from the third circumference.

In some embodiments, for example as may be shown in FIG. 12, a stent 10 may be described by the following numbered paragraphs:

1. A stent comprising a serpentine band, the serpentine band comprising a plurality of struts connected by alternating peaks and valleys, the struts including a plurality of lobed struts which have an outer surface, an inner surface and two sidewalls, one of the side walls being s-shaped, the other sidewall having a different shape.
2. The stent of paragraph 1, further comprising a plurality of serpentine bands, each serpentine band comprising alternating straight struts and lobed struts, adjacent serpentine bands connected by a connector strut.
3. The stent of paragraph 2, further comprising first serpentine bands having a first orientation and second serpentine bands having a second orientation that is different from the first orientation.

4. The stent of paragraph 3, wherein first serpentine bands and second serpentine bands alternate along the length of the stent.
5. The stent of paragraph 2, wherein the connector struts of the stent comprise first linear connectors and second linear connectors, the second linear connectors being nonparallel to the first linear connectors.
6. The stent of paragraph 5, wherein all of the first linear connectors are parallel to one another.
7. The stent of paragraph 6, wherein all of the second linear connectors are parallel to one another.
8. The stent of paragraph 5, wherein a first angle between a first linear connector and a stent lengthwise axis comprises a substantial mirror image of a second angle between a second linear connector and a stent lengthwise axis, the substantial mirror image taken across a stent circumferential line.
9. The stent of paragraph 5, wherein the first linear connectors extend from a valley of a first serpentine band to a peak of a second serpentine band.
10. The stent of paragraph 9, wherein the first linear connectors extend from the valley in a direction of a side of the valley comprising the lobed strut.
11. The stent of paragraph 9, wherein the second linear connectors extend from a valley of a second serpentine band to a peak of a first serpentine band.
12. The stent of paragraph 11, wherein the second linear connectors extend from the valley in a direction of a side of the valley comprising the straight strut.
13. The stent of paragraph 2, wherein a straight strut comprises a width, and a valley connected to the straight strut comprises a width that is greater than the width of the straight strut.
14. The stent of paragraph 2, wherein each valley of a serpentine band is aligned about a circumference of the stent.
15. The stent of paragraph 2, wherein a serpentine band comprises first peaks and second peaks, the first peaks being aligned about a first circumference of the stent, the second peaks being aligned about a second circumference of the stent that is offset from the first circumference.
16. The stent of paragraph 15, wherein the serpentine band having first peaks and second peaks further comprises first valleys and second valleys, the first valleys being aligned about a third circumference of the stent, the second valleys being aligned about a fourth circumference of the stent that is offset from the third circumference.
17. A stent comprising a serpentine band, the serpentine band including struts which have an outer surface, an inner surface and two sidewalls, one of the side walls being s-shaped, the other sidewall having a different shape.

In some embodiments, various peaks 24 and valleys 26 of a serpentine band 20 that are in area of connector struts 16 may be longitudinally offset from other peaks 24 or valleys 26 of the serpentine band 20, for example as may be shown in FIGS. 2, 3 and 17-19, and described in the following numbered paragraphs:

1. A stent comprising:
    a plurality of serpentine bands, each serpentine band comprising a plurality of struts connected by turns, the turns comprising alternating peaks and valleys;
    a plurality of connector struts, adjacent serpentine bands connected by at least one connector strut, each connector strut extending from a valley of one serpentine band to a peak of another serpentine band;
    a first serpentine band comprising a plurality of first valleys and a second valley, the first valleys being aligned about a circumference of the stent, the second valley being longitudinally offset from the first valleys;
    a second serpentine band comprising a plurality of first peaks and a second peak, the first peaks being aligned about a circumference of the stent, the second peak being longitudinally offset from the first peaks;
    wherein a first connector strut oriented at an angle to a stent lengthwise axis connects between a first valley and a first peak, the second valley being longitudinally aligned with the first peak that is connected to the first connector strut, the second peak being longitudinally aligned with the first valley that is connected to the first connector strut.
2. The stent of paragraph 1, the first serpentine band further comprising a plurality of first peaks and a second peak, the first peaks being aligned about a circumference of the stent, the second peak being longitudinally offset from the first peaks;
    the stent further comprising a third serpentine band comprising a plurality of first valleys and a second valley, the first valleys being aligned about a circumference of the stent, the second valley being longitudinally offset from the first valleys; and
    a second connector strut oriented at an angle to a stent lengthwise axis, the second connector strut connecting between a first valley of the third serpentine band and a first peak of the first serpentine band, the second valley of the third serpentine band being longitudinally aligned with the first peak that is connected to the second connector strut, the second peak of the first serpentine band being longitudinally aligned with the first valley that is connected to the second connector strut.
3. The stent of paragraph 2, wherein the first connector strut is not parallel to the second connector strut.
4. The stent of paragraph 3, wherein a first angle between the first connector strut and a stent lengthwise axis comprises a substantial mirror image of a second angle between the second connector strut and a stent lengthwise axis, the substantial mirror image taken across a stent circumferential line.
5. The stent of paragraph 1, wherein each serpentine band comprises alternating straight struts and s-shaped struts.
6. The stent of paragraph 5, wherein the first connector strut extends from a side of the first valley of the first serpentine band that comprises an s-shaped strut.
7. The stent of paragraph 6, wherein the first connector strut extends from a side of the first peak of the second serpentine band that comprises an s-shaped strut.
8. The stent of paragraph 5, wherein the second connector strut extends from a side of the first peak of the first serpentine band that comprises a straight strut.
9. The stent of paragraph 8, wherein the second connector strut extends from a side of the first valley of the third serpentine band that comprises a straight strut.
10. The stent of paragraph 1, wherein a serpentine band comprises alternating straight struts and z-shaped struts, each z-shaped strut comprising a first straight portion, a second valley, a second straight portion, a second peak and a third straight portion.
11. The stent of paragraph 10, wherein each z-shaped strut is connected to a straight strut by a first valley and connected to another straight strut by a first peak.
12. The stent of paragraph 1, wherein a serpentine band comprises alternating s-shaped struts and z-shaped struts, each z-shaped strut comprising a first straight portion, a second valley, a second straight portion, a second peak and a third straight portion.

13. The stent of paragraph 12, wherein each z-shaped strut is connected to an s-shaped strut by a first valley and connected to another s-shaped strut by a first peak.
14. The stent of paragraph 1, wherein the serpentine bands comprise first serpentine bands having a first orientation and second serpentine bands having a second orientation that is different from the first orientation.
15. The stent of paragraph 4, wherein first serpentine bands and second serpentine bands alternate along the length of the stent.
16. The stent of paragraph 1, wherein each serpentine band comprises a plurality of unconnected valleys that are not connected to a connector strut, and the width of an unconnected valley is greater than the width of a strut to which the unconnected valley is attached.

In some embodiments, a stent may comprise first serpentine bands having straight struts 30 and second serpentine bands having bent struts 32, for example as may be shown in FIG. 14 and described in the following numbered paragraphs:
1. A stent comprising:
   a plurality of first serpentine bands, each first serpentine band comprising a plurality of straight struts connected by turns, the turns comprising alternating peaks and valleys;
   a plurality of second serpentine bands, each second serpentine band comprising a plurality of bent struts connected by turns, the turns comprising alternating peaks and valleys;
   a plurality of connector struts, adjacent serpentine bands connected by at least one connector strut, each connector strut extending from a valley of one serpentine band to a peak of another serpentine band;
   wherein first and second serpentine bands alternate along the length of the stent.
2. The stent of paragraph 1, wherein a proximal end of the stent comprises a first serpentine band.
3. The stent of paragraph 2, wherein a distal end of the stent comprises a first serpentine band.
4. The stent of paragraph 1, further comprising first connector struts and second connector struts, the first connector struts being nonparallel to the second connector struts.
5. The stent of paragraph 4, wherein each first connector strut is attached to a valley of a first serpentine band.
6. The stent of paragraph 5, wherein each first connector struts is attached to a peak of a second serpentine band.
7. The stent of paragraph 4, wherein each second connector strut is attached to a valley of a second serpentine band.
8. The stent of paragraph 7, wherein each second connector struts is attached to a peak of a first serpentine band.

In some embodiments, a stent may comprise first serpentine bands having straight struts 30 and second serpentine bands having bent struts 32, for example as may be shown in FIG. 15 and described in the following numbered paragraphs:
1. A stent comprising:
   a plurality serpentine bands, each serpentine band comprising a plurality of struts connected by turns, the turns comprising alternating peaks and valleys, the serpentine bands comprising:
      a plurality of first serpentine bands, each first serpentine band comprising a plurality of straight struts connected by alternating peaks and valleys, at least one first serpentine band comprising a first peak, a plurality of second peaks, a first valley and a plurality of second valleys, the second peaks being aligned about a circumference of a stent, the first peak being longitudinally offset from the second peaks, the second valleys being aligned about a circumference of a stent, the first valley being longitudinally offset from the second valleys; and
      a plurality of second serpentine bands, each second serpentine band comprising a plurality of bent struts connected by alternating peaks and valleys, a plurality of second serpentine bands comprising a first peak, a plurality of second peaks, a first valley and a plurality of second valleys, the second peaks being aligned about a circumference of a stent, the first peak being longitudinally offset from the second peaks, the second valleys being aligned about a circumference of a stent, the first valley being longitudinally offset from the second valleys;
   wherein longitudinally adjacent serpentine bands are connected by a connection, a connection comprising a first valley that is connected to a first peak.
2. The stent of paragraph 1, wherein a proximal end of the stent comprises a first serpentine band.
3. The stent of paragraph 2, wherein a distal end of the stent comprises a first serpentine band.
4. The stent of paragraph 1, wherein each bent strut comprises a first portion that is nonparallel to a second portion.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent comprising a plurality of interconnected serpentine bands,
   each serpentine band having alternating straight struts and s-shaped struts forming peaks and valleys, each straight strut connected at one end to one s-shaped strut and at a second end to a second s-shaped strut, each s-shaped strut connected at one end to one straight strut and at a second end to a second straight strut, one end of the s-shaped struts connected to one end of the straight struts at a peak and another end of the s-shaped struts connected to one end of the straight strut at a valley,
   adjacent serpentine bands connected by a plurality of linear connectors, each linear connector extending from a peak of one serpentine band to a valley of another serpentine band adjacent thereto,
   wherein a straight strut comprises a width, and a valley connected to the straight strut comprises a width that is greater than the width of the straight strut.

2. The stent of claim 1, further comprising first serpentine bands having a first orientation and second serpentine bands having a second orientation that is different from the first orientation.

3. The stent of claim 2, wherein first serpentine bands and second serpentine bands alternate along the length of the stent.

4. The stent of claim 3, further comprising first linear connectors and second linear connectors, the second linear connectors being nonparallel to the first linear connectors.

5. The stent of claim 4, wherein all of the first linear connectors are parallel to one another.

6. The stent of claim 5, wherein all of the second linear connectors are parallel to one another.

7. The stent of claim 4, wherein the first linear connectors extend from a valley of a first serpentine band to a peak of a second serpentine band.

8. The stent of claim 7, wherein the first linear connectors extend from the valley in a direction of a side of the valley comprising the s-shaped strut.

9. The stent of claim 7, wherein the second linear connectors extend from a valley of a second serpentine band to a peak of a first serpentine band.

10. The stent of claim 9, wherein the second linear connectors extend from the valley in a direction of a side of the valley comprising the straight strut.

11. The stent of claim 1, wherein each valley of a serpentine band is aligned about a circumference of the stent.

12. The stent of claim 1, wherein the serpentine bands and the linear connectors define a plurality of cells, each cell including a plurality of unconnected peaks and valleys, the unconnected peaks disposed on one serpentine band, the unconnected valleys disposed on the adjacent serpentine band.

13. A stent comprising a plurality of interconnected serpentine bands,
   each serpentine band having alternating straight struts and s-shaped struts forming peaks and valleys, each straight strut connected at one end to one s-shaped strut and at a second end to a second s-shaped strut, each s-shaped strut connected at one end to one straight strut and at a second end to a second straight strut, one end of the s-shaped struts connected to one end of the straight struts at a peak and another end of the s-shaped struts connected to one end of the straight strut at a valley,
   the serpentine bands comprising first serpentine bands having a first orientation and second serpentine bands having a second orientation that is different from the first orientation, the first serpentine bands and second serpentine bands alternating along the length of the stent,
   adjacent serpentine bands connected by a plurality of linear connectors including first linear connectors and second linear connectors, the second linear connectors being nonparallel to the first linear connectors, each linear connector extending from a peak of one serpentine band to a valley of another serpentine band adjacent thereto,
   wherein a first angle between a first linear connector and a stent lengthwise axis comprises a substantial mirror image of a second angle between a second linear connector and a stent lengthwise axis, the substantial mirror image taken across a stent circumferential line.

14. A stent comprising a plurality of interconnected serpentine bands, each serpentine band having alternating straight struts and s-shaped struts forming peaks and valleys, each straight strut connected at one end to one s-shaped strut and at a second end to a second s-shaped strut, each s-shaped strut connected at one end to one straight strut and at a second end to a second straight strut, one end of the s-shaped struts connected to one end of the straight struts at a peak and another end of the s-shaped struts connected to one end of the straight strut at a valley, adjacent serpentine bands connected by a plurality of linear connectors, each linear connector extending from a peak of one serpentine band to a valley of another serpentine band adjacent thereto, wherein a serpentine band comprises first peaks and second peaks, the first peaks being aligned about a first circumference of the stent, the second peaks being aligned about a second circumference of the stent that is offset from the first circumference.

15. The stent of claim 14, wherein the serpentine band having first peaks and second peaks further comprises first valleys and second valleys, the first valleys being aligned about a third circumference of the stent, the second valleys being aligned about a fourth circumference of the stent that is offset from the third circumference.

16. A stent comprising a plurality of interconnected serpentine bands, each serpentine band having alternating straight struts and s-shaped struts forming peaks and valleys, each straight strut connected at one end to one s-shaped strut and at a second end to a second s-shaped strut, each s-shaped strut connected at one end to one straight strut and at a second end to a second straight strut, one end of the s-shaped struts connected to one end of the straight struts at a peak and another end of the s-shaped struts connected to one end of the straight strut at a valley, adjacent serpentine bands connected by a plurality of connectors, each connector extending from a peak of one serpentine band to a valley of another serpentine band adjacent thereto, the connectors including a first straight connector extending in a first direction and a second straight connector extending in a second direction which is non-parallel to the first direction, wherein a straight strut comprises a width, and a valley connected to the straight strut comprises a width that is greater than the width of the straight strut.

17. The stent of claim 16, wherein the first straight connector extends from a peak in a direction of a side of the peak comprising an s-shaped strut.

18. The stent of claim 17, wherein the second straight connector extends from a peak in a direction of a side of the peak comprising a straight strut.

19. A stent comprising a plurality of interconnected serpentine bands, each serpentine band having alternating straight struts and s-shaped struts forming peaks and valleys, each straight strut connected at one end to one s-shaped strut and at a second end to a second s-shaped strut, each s-shaped strut connected at one end to one straight strut and at a second end to a second straight strut, one end of the s-shaped struts connected to one end of the straight struts at a peak and another end of the s-shaped struts connected to one end of the straight strut at a valley, adjacent serpentine bands connected by a plurality of linear connectors, the connectors extending from peaks of one band to valleys of a band adjacent thereto, the serpentine bands and connectors defining a plurality of cells, each cell including a plurality of unconnected peaks and valleys, the unconnected peaks disposed on one serpentine band, the unconnected valleys disposed on the adjacent serpentine band, wherein a straight strut comprises a width, and a valley connected to the straight strut comprises a width that is greater than the width of the straight strut.

* * * * *